United States Patent [19]

Petrzilka et al.

[11] 4,432,885
[45] Feb. 21, 1984

[54] DECALINS

[75] Inventors: Martin Petrzilka, Kaiseraugst; Kuno Schleich, Zollikerberg, both of Switzerland

[73] Assignee: Hoffmann-La Roche Inc., Nutley, N.J.

[21] Appl. No.: 328,979

[22] Filed: Dec. 9, 1981

[30] Foreign Application Priority Data

Dec. 23, 1980 [CH] Switzerland ............... 9524/80
Aug. 26, 1981 [CH] Switzerland ............... 5513/81

[51] Int. Cl.³ .................. C07C 43/116; C07C 49/30;
C07C 63/00; C07C 69/76; C07C 103/22;
C07C 121/64; C07C 13/50; C07C 25/02;
C07C 13/47; C09C 3/34; C09K 3/34
[52] U.S. Cl. .................. 252/299.61; 252/299.62;
252/299.63; 350/350 R; 260/464; 260/465 C;
260/465 D; 260/465 F; 260/465 R; 560/1;
560/17; 560/56; 560/116; 560/139; 560/141;
562/466; 562/469; 562/492; 562/499
[58] Field of Search ............. 252/299.61, 299.62,
252/299.63; 350/350 R; 260/464, 465 C, 465 D,
465 F, 465 R; 560/1, 17, 56, 116, 139, 141;
562/466, 469, 492, 499

[56] References Cited

U.S. PATENT DOCUMENTS

| 3,925,237 | 12/1975 | Ross et al. . | |
|---|---|---|---|
| 4,119,558 | 10/1978 | Coates et al. . | |
| 4,386,007 | 5/1983 | Krause et al. | 252/299.62 |
| 4,391,731 | 7/1983 | Boller et al. | 252/299.62 |

FOREIGN PATENT DOCUMENTS

| 25598 | 3/1981 | European Pat. Off. | 252/299.62 |
|---|---|---|---|
| 2949080 | 6/1981 | Fed. Rep. of Germany . | |
| 3201721 | 8/1982 | Fed. Rep. of Germany | 252/299.62 |
| 56-46855 | 4/1981 | Japan | 252/299.62 |
| 56-108740 | 8/1981 | Japan | 252/299.62 |
| 57-54130 | 3/1982 | Japan | 252/299.62 |
| 1240911 | 7/1971 | United Kingdom . | |
| 1531405 | 11/1978 | United Kingdom . | |
| 2082179 | 3/1982 | United Kingdom | 252/299.62 |
| 2084576 | 4/1982 | United Kingdom | 252/299.62 |

OTHER PUBLICATIONS

"Substituted 2-Phenylnaphthalenes, a New Class of Nematic Liquid Crystals", Lauk et al., *Helvetica Chimica Acta,* vol. 64 (1981) #176.
Chemical Abstracts, vol. 80, 1974 #120620a.
Coates et al., Mol. Cryst. Liq. Cryst. 37, 249–262 (1976).
Coates et al., Mol. Cryst. Liq. Cryst. 41, 119–124 (1978).
Lauk et al., Helv. Chim. Acta. 64, 1847 (1981).
Gysin; E., Helvetica Chim. Acta 9, 59–67 (1926 and its Chem. Abst. 20:1402.
Chem. Abst. 95:1151356 (1981).

*Primary Examiner*—Teddy S. Gron
*Assistant Examiner*—Catherine S. Kilby
*Attorney, Agent, or Firm*—Jon S. Saxe; Bernard S. Leon; George W. Johnston

[57] ABSTRACT

Decalins of the formula

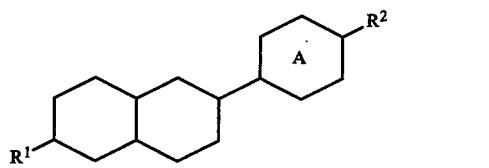

wherein ring A is aromatic or a trans-1,4-disubstituted cyclohexane ring; $R^2$ is methyl, —CH$_2$R', —OR', —CO—R', —CN, —COOH, —CO—OR', —CO—SR' or —O—CO—R'; $R^1$ is hydrogen, methyl, —CH$_2$R, —OR or —CH$_2$OR, or when $R^2$ is methyl, —CH$_2$R', —OR' or —CO—R', $R^1$ also can be —CN, —COOH, —CO—OR, —CO—SR or —O—CO—R; R and R' each are alkyl; and $R^1$ and $R^2$ each have up to 12 carbon atoms and together have at most 14 carbon atoms, their racemates and optically active antipodes, are described. Liquid crystalline mixtures comprising Compound I as well as their use in electro-optical devices also are disclosed.

18 Claims, No Drawings

DECALINS

BACKGROUND OF THE INVENTION

1. Field of the Invention

This invention relates to liquid crystalline compounds and mixtures.

2. Description of the State of the Art

In an electric field, the molecules of liquid crystalline compounds and mixtures which possess a positive anisotropy of the dielectric constants (i.e., $\epsilon_\| > \epsilon_\perp$) are oriented with their longitudinal axes parallel to the field direction. $\epsilon_\|$ signifies the dielectric constant along the longitudinal axis of the molecule and $\epsilon_\perp$ signifies the dielectric constant perpendicular thereto.

This dielectric field effect is utilized in the interaction between the liquid crystalline molecules and guest molecules (guest-host interaction) described by J. H. Heilmeier and L. A. Zanoni [Applied Physics Letter 13, 91 (1968)]. Another application of the dielectric field effect is the electro-optical rotation cell discovered by M. Schadt and W. Helfrich [Applied Physics Letter 18 (1971)]. A further example is the Kerr cell described in Molecular Crystals and Liquid Crystals 17, 355 (1972).

The above electro-optical rotation cell includes a condenser-like structure having transparent electrode plates, the dielectric of which is formed from nematic liquid crystal material with $\epsilon_\| > \epsilon_\perp$. The longitudinal axes of the liquid crystal molecules are arranged in twisted or helical form between the plates in the fieldless state. The twisting structure is determined by the given wall orientation of the molecules. After applying an electric potential to the condenser plates, the molecules adjust themselves with their longitudinal axes in the field direction, i.e., perpendicular to the surface of the plates, so that linear polarized light no longer rotates in the dielectric (the liquid crystal is uniaxially perpendicular to the surface of the plates). After removing the electric potential, the molecules return to their prior orientation. This reversible effect on the molecules can be used to electrically control the optical transmissivity of the condenser. To achieve an optimal transition between these two orientations, the threshold potential of the compounds or mixtures can be adjusted to the driving potential of the rotation cell. The driving potential of such a "light rotation cell" is dependent on the battery potential and the control circuit used. It becomes desirable to utilize liquid crystalline mixtures having low threshold potentials.

Further, a mixture of nematic liquid crystals with positive anisotropy and cholesteric substances (or generally soluble, optically active substances provided the total mixture remains liquid crystalline) undergoes a phase transition upon application of an electric field. This phase change effect is reversible and makes it possible to have high switching speeds of electro-optical devices which operate with such mixtures. By selecting the concentration of cholesteric additives in a liquid crystal mixture, one attempts to improve the electro-optical properties of rotational cells.

It also is known that liquid crystalline mixtures with low viscosities have short response times.

We have invented liquid crystalline compounds and mixtures which advantageously possess low threshold potentials, good chemical stability and ready orientability.

SUMMARY OF THE INVENTION

The invention relates to decalins of the formula

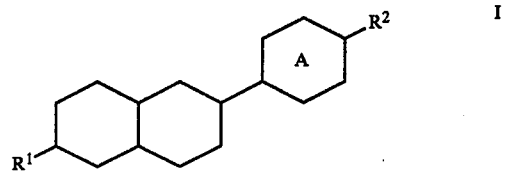

wherein ring A is aromatic or a trans-1,4-disubstituted cyclohexane ring; $R^2$ is methyl, —$CH_2R'$, —OR', —CO—R', —CN, —COOH, —CO—OR', —CO—SR' or —O—CO—R'; $R^1$ is hydrogen, methyl, —$CH_2R$, —OR or —$CH_2OR$ or, when $R^2$ is methyl, —$CH_2R'$, —OR' or —CO—R', $R^1$ can also be —CN, —COOH, —CO—OR, —CO—SR or —O—CO—R; and R and R' each are alkyl.

The $R^1$ and $R^2$ moieties each contain up to 12 carbon atoms. The sum of the carbon atoms in $R^1$ and $R^2$ is at most 14. Racemates and optically active compounds are included within formula I.

The inventive compounds are useful in electro-optical apparatuses and possess especially low threshold voltages as well as low viscosities.

The invention further is concerned with liquid crystal compounds, mixtures, processes, uses and apparatuses as described below.

DETAILED DESCRIPTION OF THE INVENTION

The present invention relates to equatorially substituted trans-decalins of the formula

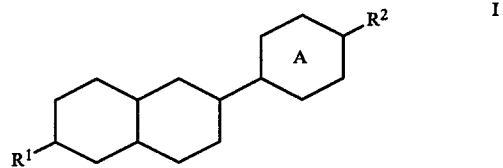

wherein ring A is aromatic or a trans-1,4-disubstituted cyclohexane ring; $R^2$ is methyl, —$CH_2R'$, —OR', —CO—R', —CN, —COOH, —CO—OR', —CO—SR' or —O—CO—R'; $R^1$ is hydrogen, methyl, —$CH_2R$, —OR or —$CH_2OR$; and R and R' each are straight-chain or branched-chain alkyl. In addition to the previously mentioned moieties for $R^1$, when $R^2$ is methyl, —$CH_2R'$, —OR', or —CO—R', $R^1$ also can be —CN, —COOH, —CO—OR, —CO—SR or O—CO—R. Additionally, the $R^1$ and $R^2$ groups can be the same or different and each contain up to 12 carbon atoms but together contain at most 14 carbon atoms. The racemates and optical antipodes of Compound I are part of the invention.

Compound I has at least 3 (or 4 where $R^1$ is other than hydrogen) asymmetric carbon atoms. Throughout the specification, the representation of the decalin structure as used in formula I (and hereinafter also for starting materials) signifies trans-decalins with an equatorial arrangement of the substituents. Compound I accordingly embraces compounds of the formulas

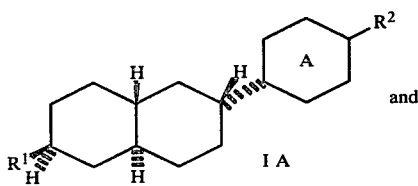

and

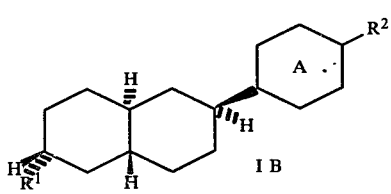

wherein R¹, R² and ring A are as above and the symbol ▬ indicates that the corresponding bond to the substituent or hydrogen atom is directed upwards (above the plane of the drawing, β-configuration) and the symbol ||  ||  || indicates that the corresponding bond to the substituent or hydrogen atom is directed downwards (below the plane of the drawing, α-configuration).

The inventive compounds thus include optically active compounds of formulas IA or IB or mixtures of corresponding compounds of formulas IA and IB, especially as 1:1 mixtures. When one or both of R¹ or R² signifies an optically active group, the 1:1 mixtures are also optically active; otherwise they are optically inactive.

Compound I (especially wherein R¹ and R² each are alkyl), generally exhibit a large mesophase range and low viscosity. Moreover, the inventive compounds have good chemical stability, ready orientability and slight smectic tendencies. Further, they are colorless and exhibit a high UV-stability.

The dielectric anisotropy essentially is dependent upon the nature of R¹ and R² within Compound I. For example, the compounds of formula I in which one of R¹ and R² is cyano have a high positive anisotropy of the dielectric constants. Those compounds in which R¹ is alkyl and R² is alkyl or alkanoyl have a small anisotropy of the dielectric constants. By suitable selections for R¹ and R² within Compound I, one extensively can adjust the threshold potential of liquid crystalline mixtures which are used in electro-optical cells.

Compound I in which R¹ or R² is carboxyl have particularly large mesophase ranges and high clearing points, but at the same time also have high viscosities. On the other hand, Compound I in which R¹ is hydrogen generally is not liquid crystalline. Such compounds, however, are suitable as doping agents in liquid crystal mixtures and often exhibit surprisingly low melting points.

Unless otherwise stated, "alkyl" denotes a straight-chain alkyl group of 1 to 12 carbon atoms or a branched-chain alkyl group of 1 to 12 carbon atoms. Exemplary straight-chain alkyl groups are methyl, ethyl, propyl, butyl, pentyl, hexyl, heptyl, octyl, nonyl, decyl, undecyl and dodecyl. Exemplary branched chain alkyl groups are isopropyl, isobutyl, sec-butyl, 1-methylbutyl, 2-methylbutyl and isopentyl. Lower alkyl denotes straight-chain and branched-chain alkyl groups of 1 to 5 carbon atoms. The term "primary alkyl" denotes a group of the formula —CH₂R‴ wherein R‴ is alkyl as defined above.

As noted above, —R and —R' each are alkyl. In particular, —R and —R' embrace straight-chain alkyl groups and branched-chain alkyl groups including branched-chain alkyl groups of the formula $C_2H_5$—$CH(CH_3)$—$(CH_2)_n$— in which n is 0, 1, 2 or 3. Such branched-chain alkyl groups are sec-butyl, 2-methylbutyl, 3-methylpentyl and 4-methylhexyl.

The terms "alkoxy" (—OR), "alkanoyl" (—CO—R), "alkoxycarbonyl" (—CO—OR), "alkylthiocarbonyl" (—CO—SR) and "alkanoyloxy" (—O—CO—R) denote moieties in which its "alkyl" portion is as defined previously.

The term "aromatic" means a phenyl ring.

The term "readily cleavable alcohol protecting group" includes those alcohol protecting groups which can be cleaved off under conditions which do not affect an alkoxy group.

In a preferred aspect of the invention, the decalins of formula I include compounds wherein one or both of the R and R' groups is straight-chain alkyl or branched-chain alkyl of the formula $C_2H_5$—$CH(CH_3)$—$(CH_2)_n$—, and n is an integer of 0 to 3.

In another preferred embodiment for Compound I one of R¹ and R² at most contains a branched-chain alkyl group for R or R'. Especially preferred are those compounds of formula I wherein one or both of R and R' is straight-chain alkyl.

Preferred R¹ groups within Compound I are methyl, —CH₂R and —OR, especially methyl and —CH₂R wherein R is as above. Preferred R² groups are methyl, —CH₂R', —OR', —CO—R', —CN, —COOR' and —O—CO—R', and especially methyl, —CH₂R', —CN and —CO— R' wherein R' is as above. Ring A is preferably aromatic.

Further, the groups R¹ or R² containing up to 9 carbon atoms are preferred and those containing up to 7 carbon atoms are especially preferred. The particularly preferred values for R¹ are propyl, butyl, pentyl and heptyl and particularly preferred values for R² are cyano, propyl and pentyl.

Furthermore, there are preferred principally those compounds of formula I which are present as a mixture of compounds of formula IA and the corresponding compounds of formula IB, especially the 1:1 mixture. Consequently, the optically inactive (racemic) compounds of formula I are especially preferred.

The following are preferred compounds of the formula I:

(4aαH,8aβH)-Decahydro-2α-(p-methylphenyl)-6β-pentylnaphthalene, (4aαH,8aβH)-decahydro-2α-(p-methylphenyl)-6β-heptylnaphthalene, (4aαH,8aβH)-decahydro-2α-(p-ethylphenyl)-6β-propylnaphthalene, (4aαH,8aβH)-decahydro-2α-(p-ethylphenyl)-6β-pentylnaphthalene, (4aαH,8aβH)-decahydro-2α-(p-propylphenyl)-6β-propylnaphthalene, (4aαH,8aβH)-decahydro-2α-(p-propylphenyl)-6β-pentylnaphthalene, (4aαH,8aβH)-decahydro-2α-(p-propylphenyl)-6β-heptylnaphthalene, (4aαH,8aβH)-decahydro-2α-(p-butylphenyl)-6β-propylnaphthalene, 4aαH,8aβH)-decahydro-2α-(p-butylphenyl)-6β-pentylnaphthalene, (4aαH,8aβH)-decahydro-2α-(p-pentylphenyl)-6β-propylnaphthalene, (4aαH,8aβH)-decahydro-2α-(p-pentylphenyl)-6β-pentylnaphthalene,
(4aαH,8aβH)-decahydro-2α-(p-pentylphenyl)-6β-heptylnaphthalene, (4aαH,8aβH)-decahydro-2α-(p-heptylphenyl)-6β-propylnaphthalene,
(4aαH,8aβH)-decahydro-2α-(trans-4-methylcyclohexyl)-6β-propylnaphthalene,
(4aαH,8aβH)-decahydro-2α-(trans-4-methylcyclohexyl)-6β-pentylnaphthalene,
(4aαH,8aβH)-decahydro-2α-(trans-4-methylcyclohexyl)-6β-heptylnaphthalene,
(4aαH,8aβH)-decahydro-2α-(trans-4-propylcyclohexyl)-6β-propylnaphthalene,
(4aαH,8aβH)-decahydro-2α-(trans-4-propylcyclohexyl)-6β-pentylnaphthalene,
(4aαH,8aβH)-decahydro-2α-(trans-4-propylcyclohexyl)-6β-heptylnaphthalene,
(4aαH,8aβH)-decahydro-2α-(trans-4-pentylcyclohexyl)-6β-methylnaphthalene,
(4aαH,8aβH)-decahydro-2α-(trans-4-pentylcyclohexyl)-6β-propylnaphthalene,
(4aαH,8aβH)-decahydro-2α-(trans-4-pentylcyclohexyl)-6β-pentylnaphthalene,
(4aαH,8aβH)-decahydro-2α-(trans-4-pentylcyclohexyl)-6β-heptylnaphthalene,
(4aαH,8aβH)-decahydro-2α-(trans-4-heptylcyclohexyl)-6β-propylnaphthalene,
4'-[(4aαH,8aβH)-decahydro-6β-methyl-2α-naphthyl]-propiophenone,
4'-[(4aαH,8aβH)-decahydro-6β-methyl-2α-naphthyl]-valerophenone,
4'-[(4aαH,8aβH)-decahydro-6β-ethyl-2α-naphthyl]-valerophenone,
4'-[(4aαH,8aβH)-decahydro-6β-propyl-2α-naphthyl]-acetophenone,
4'-[(4aαH,8aβH)-decahydro-6β-propyl-2α-naphthyl]-propiophenone,
4'-[(4aαH,8aβH)-decahydro-6β-propyl-2α-naphthyl]-butyrophenone,
4'-[(4aαH,8aβH)-decahydro-6β-propyl-2α-naphthyl]-valerophenone,
4'-[(4aαH,8aβH)-decahydro-6β-propyl-2α-naphthyl]-hexanophenone,
4'-[(4aαH,8aβH)-decahydro-6β-propyl-2α-naphthyl]heptanophenone,
4'-[(4aαH,8aβH)-decahydro-6β-butyl-2α-naphthyl]-valerophenone,
4'-[(4aαH,8aβH)-decahydro-6β-pentyl-2α-naphthyl]-acetophenone,
4'-[(4aαH,8aβH-decahydro-6β-pentyl-2α-naphthyl]-propiophenone,
4'-[(4aαH,8aβH)-decahydro-6β-pentyl-2α-naphthyl]-butyrophenone,
4'[(4aαH,8aβH)-decahydro-6β-pentyl-2α-naphthyl]-valerophenone,
4'[(4aαH,8aβH)-decahydro-6β-heptyl-2α-naphthyl]-propiophenone,
(4aαH,8aβH)-decahydro-2α-(trans-4-acetylcyclohexyl)-6β-propylnaphthalene,
(4aαH,8aβH)-decahydro-2α-(trans-4-propionylcyclohexyl)-6β-propylnaphthalene,
(4aαH,8aβH)-decahydro-2α-(trans-4-valerylcyclohexyl)-6β-propylnaphthalene,
(4aαH,8aβH)-decahydro-2α-(trans-4-heptanoylcyclohexyl)-6β-propylnaphthalene,
(4aαH,8aβH)-decahydro-2α-(trans-4-propionylcyclohexyl)-6β-butylnaphthalene,
(4aαH,8aβH)-decahydro-2α-(trans-4-acetylcyclohexyl)-6β-pentylnaphthalene,
(4aαH,8aβH)-decahydro-2α-(trans-4-propionylcyclohexyl)-6β-pentylnaphthalene,
(4aαH,8aβH)-decahydro-2α-(trans-4-butyrylcyclohexyl)-6β-pentylnaphthalene,
(4aαH,8aβH)-decahydro-2α-(trans-4-valerylcyclohexyl)-6β-pentylnaphthalene,
(4aαH,8aβH)-decahydro-2α-(trans-4-heptanoylcyclohexyl)-6β-pentylnaphthalene,
(4aαH,8aβH)-decahydro-2α-(trans-4-propionylcyclohexyl)-6β-heptylnaphthalene,
(4aαH,8aβH)-decahydro-2α-(p-ethoxyphenyl)-6β-pentylnaphthalene,
(4aαH,8aβH)-decahydro-2α-(p-propyloxyphenyl)-6β-pentylnaphthalene,
(4aαH,8aβH)-decahydro-2α-(p-butyloxyphenyl)-6β-propylnaphthalene,
(4aαH,8aβH)-decahydro-2α-(p-butyloxyphenyl)-6β-pentylnaphthalene,
(4aαH,8aβH)-decahydro-2α-(p-hexyloxyphenyl)-6β-propylnaphthalene,
(4aαH,8aβH)-decahydro-2α-(trans-4-butyloxycyclohexyl)-6β-propylnaphthalene,
(4aαH,8aβH)-decahydro-2α-(trans-4-butyloxycyclohexyl)-6β-pentylnaphthalene,
p-[(4aαH,8aβH)-decahydro-6β-methyl-2α-naphthyl]-benzonitrile,
p-[(4aαH,8aβH)-decahydro-6β-ethyl-2α-naphthyl]-benzonitrile,
p-[(4aαH,8aβH)-decahydro-6β-propyl-2α-naphthyl]-benzonitrile,
p-[(4aαH,8aβH)-decahydro-6β-butyl-2α-naphthyl]-benzonitrile,
p-[(4aαH,8aβH)-decahydro-6β-pentyl-2α-naphthyl]-benzonitrile,
p-[(4aαH,8aβH)-decahydro-6β-hexyl-2α-naphthyl]-benzonitrile,
p-[(4aαH,8aβH)-decahydro-6β-heptyl-2α-naphthyl]-benzonitrile,
trans-4-[(4aαH,8aβH)-decahydro-6β-methyl-2α-naphthyl]cyclohexanecarbonitrile,
trans-4-[(4aαH,8aβH)-decahydro-6β-ethyl-2α-naphthyl]cyclohexanecarbonitrile,
trans-4-[(4aαH,8aβH)-decahydro-6β-propyl-2α-naphthyl]cyclohexanecarbonitrile,
trans-4-[(4aαH,8aβH)-decahydro-6β-butyl-2α-naphthyl]cyclohexanecarbonitrile,
trans-4-[(4aαH,8aβH)-decahydro-6β-pentyl-2α-naphthyl]cyclohexanecarbonitrile,
trans-4-[(4aαH,8aβH)-decahydro-6β-heptyl-2α-naphthyl]cyclohexanecarbonitrile,
p-[(4aαH,8aβH)-decahydro-6β-propyl-2α-naphthyl]-benzoic acid,
p-[(4aαH,8aβH)-decahydro-6β-pentyl-2α-naphthyl]-benzoic acid,
trans-4-[(4aαH,8aβH)-decahydro-6β-propyl-2α-naphthyl]cyclohexanecarboxylic acid,
trans-4-[(4aαH,8aβH)-decahydro-6β-pentyl-2α-naphthyl]cyclohexanecarboxylic acid,
p-[(4aαH,8aβH)-decahydro-6β-propyl-2α-naphthyl]-benzoic acid methyl ester,
p-[(4aαH,8aβH)-decahydro-6β-pentyl-2α-naphthyl]-benzoic acid methyl ester,
p-[(4aαH,8aβH)-decahydro-6β-pentyl-2α-naphthyl]-benzoic acid ethyl ester,
p-[(4aαH,8aβH)-decahydro-6β-pentyl-2α-naphthyl]-benzoic acid propyl ester, p-[(4αH,8αβH)-decahydro-6β-heptyl-2α-naphthyl]-benzoic acid methyl ester, p-[(4αH,8αβH)-decahydro-6β-pentyl-2α-naphthyl]-benzoic acid methylthio ester, trans-4-[(4αH,8αβH)-decahydro-6β-pentyl-2α-naphthyl]cyclohexanecarboxylic acid methyl ester, trans-4-[(4αH,8αβH)-decahydro-6β-pentyl-2α-naphthyl]cyclohexanecarboxylic acid propyl ester, p-[(4αH,8αβH)-decahydro-6β-propyl-2α-naphthyl]-phenylacetate, p-[(4αH,8αβH)-decahydro-6β-pentyl-2α-naphthyl]-phenylacetate, p-[(4αH,8αβH)-decahydro-6β-pentyl-2α-naphthyl]-phenylpropionate, p-[(4αH,8αβH)-decahydro-6β-pentyl-2α-naphthyl]-phenylbutyrate, p-[(4αH,8αβH)-decahydro-6β-heptyl-2α-naphthyl]-phenylacetate, trans-4-[(4αH,8αβH)-decahydro-6β-pentyl-2α-naphthyl]cyclohexylacetate, trans-4-[(4αH,8αβH)-decahydro-6β-pentyl-2α-naphthyl]cyclohexylbutyrate, (4αH,8αβH)-decahydro-2α-(p-propylphenyl)naphthalene, (4αH,8αβH)-decahydro-2α-(p-pentylphenyl)naphthalene, 4'-[(4αH,8αβH)-decahydro-2α-naphthyl]propiophenone, 4'-[(4αH,8αβH)-decahydro-2α-naphthyl]valerophenone, p-[(4αH,8αβH)-decahydro-2α-naphthyl]benzonitrile, (4αH,8αβH)-decahydro-2β-(p-butyloxyphenyl)-naphthalene, (4αH,8αβH)-decahydro-2α-(trans-4-pentylcyclohexyl)naphthalene, (4αH,8αβH)-decahydro-2α-(trans-4-valerylcyclohexyl)naphthalene, (4αH,8αβH)-decahydro-2α-(p-propylphenyl)-6β-butyloxynaphthalene, (4αH,8αβH)-decahydro-2α-(p-pentylphenyl)-6β-butyloxynaphthalene, 4'-[(4αH,8αβH)-decahydro-6β-butyloxy-2α-naphthyl]-acetophenone, 4'-[(4αH,8αβH)-decahydro-6β-butyloxy-2α-naphthyl]-valerophenone, (4αH,8αβH)-decahydro-2α-(p-butyloxyphenyl)-6β-butyloxynaphthalene, p-[(4αH,8αβH)-decahydro-6β-ethoxy-2α-naphthyl]benzonitrile, p-[(4αH,8αβH)-decahydro-6β-butyloxy-2α-naphthyl]benzonitrile, as well as their optical antipodes and racemates.

In accordance with the invention, Compound I can be manufactured as follows:

(a) for Compound I in which R² is methyl or —CH₂R' and R' is as above, reducing a compound of the formula

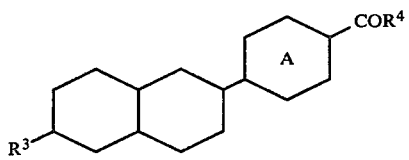

wherein R³ is hydrogen, methyl, —CH₂R, —OR, —OR", —CH₂OR or —CH₂OR", R⁴ is hydrogen or alkyl, R" is a readily cleavable alcohol protecting group and R, R' and ring A are as above, cleaving off R" (if present) and esterifying the resulting hydroxy group to —O—CO—R or oxidizing the resulting hydroxymethyl group to the carboxyl group and if desired, converting the carboxyl group into —CO—OR, —CO—SR or —CN where R is as above;

(b) for Compound I in which R² is —CH₂R' and R¹ is —CN, —COOH, —CO—OR, —CO—SR or —O—CO—R and R' is as above, reducing a compound of the formula

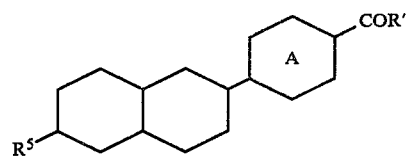

wherein R⁵ is —COOH, —CO—OR or —O—CO—R and R, R' and ring A are as above, and, if desired, converting the carboxyl group for R⁵ into —CO—OR, —CO—SR or —CN where R is as above;

(c) for Compound I in which R² is methyl, reducing the tosylate of a compound of the formula

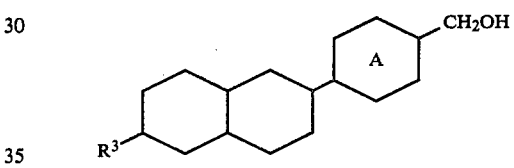

wherein R³ is hydrogen, methyl, —CH₂R, —OR, —OR", —CH₂OR or —CH₂OR", R" is a readily cleavable alcohol protecting group, and R and ring A are as above, cleaving off R" (if present) and esterifying the resulting hydroxy group to —O—CO—R or oxidizing the resulting hydroxymethyl group to the carboxyl group and, if desired, converting the carboxyl group into —CO—OR, —CO—SR or —CN where R is as above;

(d) for Compound I in which R² is alkoxy —OR' and R' is as above, etherifying a compound of the formula

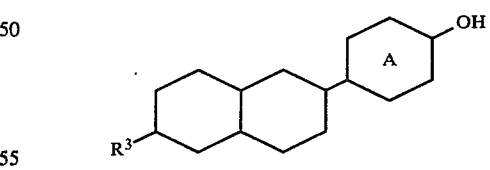

wherein R³ is hydrogen, methyl, —CH₂R, —OR, —OR", —CH₂OR or —CH₂OR", R" is a readily cleavable alcohol protecting group and R, R' and ring A are as above, cleaving off R" (if present) and esterifying the resulting hydroxy group to —O—CO—R or oxidizing the resulting hydroxymethyl group to the carboxyl group and, if desired, converting the carboxyl group into —CO—OR, —CO—SR or —CN wherein R is as above;

(e) for Compound I in which R² is alkanoyl —CO—R', R' is as above and ring A is aromatic, reacting a compound of the formula

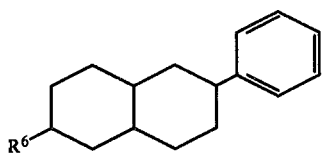

IVa wherein $R^6$ is hydrogen, methyl, —$CH_2R$, —OR, —$CH_2OR$, —CO—OR or —O—CO—R and R and R' are as above, with a carboxylic acid chloride, bromide or anhydride in the presence of a Lewis acid, preferably aluminium trichloride, if desired, hydrolyzing —CO—OR for $R^1$ and, if desired, converting the resulting carboxyl group into —CO—SR or —CN wherein R is as above;

(f) for Compound I in which $R^2$ is alkanoyl —CO—R', R' is as above and ring A is a trans-1,4-disubstituted cyclohexane ring, oxidizing a compound of the formula

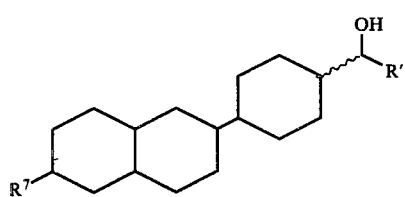

Va wherein $R^7$ is hydrogen, methyl, —$CH_2R$, —OR, —$CH_2OR$, —COOH, —CO—OR or —O—CO—R, the notation " " indicates that the 1-hydroxyalkyl group of Compound Va can have the cis-trans-configuration and R and R' are as above, if desired, subsequently equilibrating under basic conditions and esterifying the hydroxy group (which may be obtained from the group —O—CO—R) to —O—CO—R or, if desired, converting the carboxyl group into —CO—OR, —CO—SR or —CN where R is as above;

(g) for Compound I in which $R^2$ is cyano, dehydrating a compound of the formula

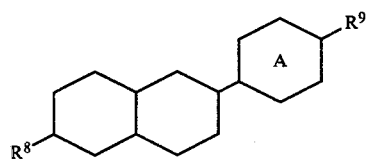

VIa wherein $R^8$ is hydrogen, methyl, —$CH_2R$, —OR or —$CH_2OR$, $R^9$ is —$CONH_2$ or —CH=N—OH and R and ring A are as above;

(h) for Compound I in which $R^2$ is cyano and ring A is aromatic, reacting a compound of the formula

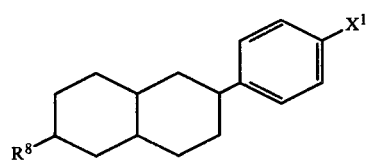

VIIa wherein $R^8$ is hydrogen, methyl, —$CH_2R$, —OR or —$CH_2OR$, $X^1$ is bromine or iodine and R is as above, with copper (I) cyanide sodium cyanide or potassium cyanide;

(i) for Compound I in which $R^2$ is carboxyl, oxidizing a compound of the formula

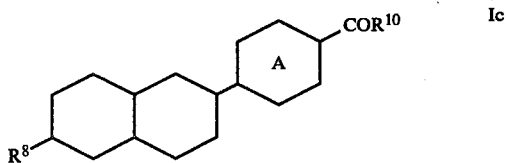

Ic wherein $R^8$ is hydrogen, methyl, —$CH_2R$, —OR or —$CH_2OR$, $R^{10}$ is hydrogen or methyl and R and ring A are as above;

(j) for Compound I in which $R^2$ is ester groups —CO—OR' or —CO—SR' and R' is as above, esterifying a compound of the formula

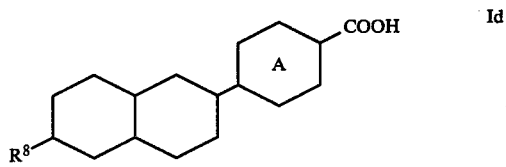

Id wherein $R^8$ is hydrogen, methyl, —$CH_2R$, —OR or —$CH_2OR$ and R, R' and ring A are as above, or a reactive derivative thereof with a compound of the formula R'—XH, wherein R' is alkyl and X is oxygen or sulphur, or a suitable salt thereof;

(k) for Compound I in which $R^2$ is alkanoyloxy —O—CO—R' and R' is as above, especially R' being methyl or primary alkyl, reacting a compound of the formula

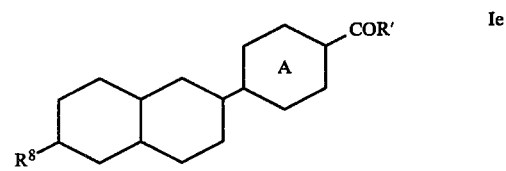

Ie wherein $R^8$ is hydrogen, methyl, —$CH_2R$, —OR or —$CH_2OR$ and R, R' and ring A are as above, with a peracid;

(l) for Compound I in which $R^2$ is alkanoyloxy —O—CO—R' and R' is as above, esterifying a compound of the formula

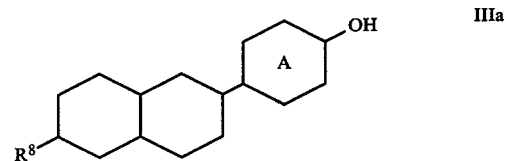

IIIa wherein $R^8$ is hydrogen, methyl, —$CH_2R$, —OR or —$CH_2OR$ and R, R' and ring A are as above, or a suitable salt thereof with a carboxylic acid of the formula R'—COOH, and R' is as above, or a reactive derivative thereof;

(m) for Compound I in which ring A is aromatic, $R^2$ is methyl, —$CH_2R'$ or —OR' and $R^1$ is alkanoyloxy —O—CO—R, and R' and R as above, esterifying a compound of the formula

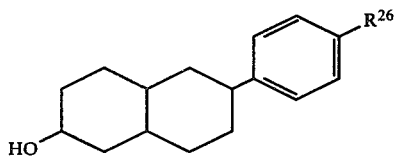

VLII wherein $R^{26}$ is methyl, —$CH_2R'$ or —$OR'$ and $R'$ is as above, or a suitable salt thereof;
and/or (n) for Compound I in which ring A is aromatic, $R^2$ is methyl, —$CH_2R'$ or —$OR'$ and $R^1$ is alkoxy —OR and $R'$ and R are as above, etherifying Compound VLII.

The number of carbon atoms which can be present in the groups R and $R'$ of the aforementioned starting materials is evident from the definition of the products defined by formula I.

Preferred examples of readily cleavable alcohol protecting groups for $R''$ are benzyl, tetrahydropyranyl [Adv. Org. Chem. 3 (1963) 216], —$CH_2OCH_3$ [J. Amer. Chem. Soc. 99, 1275 (1977)] and —$CH_2OCH_2CH_2OCH_3$ (Tetrahedron Letters 1976, 809), t-butyl-dimethyl-silyl [J. Amer. Chem. Soc. 94, 6190 (1972)] and the like. Illustratively, the benzyl group can be cleaved off by catalytic hydrogenation (under the same conditions as described hereinafter for the hydrogenation of the compounds of formula Ia in which ring A is aromatic) and palladium/carbon is the preferred catalyst. The groups —$CH_2OCH_3$, tetrahydropyranyl and t-butyl-dimethyl-silyl can be removed by reaction with a strong acid such as sulphuric acid, hydrochloric acid, p-toluenesulphonic acid and the like. Illustratively, —$CH_2OCH_2CH_2OCH_3$ can be removed by reaction with zinc (II) bromide or titanium (IV) chloride in methylene chloride at about room temperature. The t-butyl-dimethyl-silyl group can also be cleaved off by reaction with a fluoride, preferably an alkali metal fluoride or a tetraalkylammonium fluoride such as potassium fluoride, tetrabutylammonium fluoride and the like. The introduction of the aforementioned protecting groups can be carried out by reacting the alcohol to be protected with benzyl chloride, dihydropyran, chloromethyl methyl ether, β-methoxyethoxy-methyl chloride, t-butyl-dimethyl-silyl chloride and the like, if desired in the presence of a base or an acid (e.g. sodium hydride, triethylamine, imidazole, p-toluene sulfonic acid). A detailed description relating to the introduction and cleavage of alcohol protecting groups is present in the literature mentioned earlier.

In above process (a), the reduction of the carbonyl group in Compound Ia to the methylene group can be carried out according to known methods. For example, Compound Ia can be reacted with hydrazine in the presence of a base (e.g., potassium hydroxide, sodium ethylate, potassium t-butylate and the like) in an inert organic solvent (e.g., dimethyl sulphoxide) or an alcohol (e.g., ethanol, diethyleneglycol, triethylglycol and the like). Subsequently, the resulting hydrazone can be decomposed by conventional techniques. In general, the hydrazone is decomposed at an elevated temperature (e.g., at about 200° C.). If dimethyl sulphoxide is used as the solvent, then the decomposition frequently occurs at about room temperature. In a preferred embodiment, the reduction is carried out according to the Huang-Minlon process. By this process, one heats the ketone or aldehyde of Compound Ia under reflux in a high-boiling solvent which is miscible with water (e.g., diethyleneglycol or triethyleneglycol) together with hydrazine hydrate and potassium hydroxide, subsequently distills off the water until the hydrazone decomposes and continues the boiling under reflux until the reduction is completed.

An additional method for reducing Compound Ia under process (a) comprises reacting said compounds with an alkanethiol or alkanedithiol (e.g., ethanethiol, 1,3-propanedithiol, ethanedithiol and the like) and subsequently cleaving the resulting thioketal by catalytic hydrogenation with Raney-nickel. Preferred thiols which give cyclic thioketals are 1,3-propanedithiol and especially ethanedithiol. The formation of the thioketal can be catalyzed, for example, with boron trifluoride etherate. Conveniently, the preparation of the thioketal and the hydrogenation are carried out in an inert organic solvent such as diethyl ether, dioxan, methylene chloride and the like. However, when the thiol is a liquid, it can also simultaneously serve as the solvent. The pressure and temperature are not critical and atmospheric pressure and about room temperature conveniently are used.

Further, under process (a) the aldehydes and ketones of Compound Ia can be reduced (e.g., with lithium aluminium hydride in diethyl ether, sodium borohydride in ethanol or water, lithium borohydride in diethyl ether or tetrahydrofuran and the like) to corresponding alcohols. The resulting compounds can be converted into corresponding tosylates and the tosylates can be reductively cleaved by conventional techniques. The preparation of the tosylates is conveniently carried out in an inert organic solvent such as diethyl ether, tetrahydrofuran, benzene, cyclohexane, carbon tetrachloride and the like. Tosyl chloride is the preferred reagent.

In order to bind the hydrogen chloride which is liberated in the above reaction, an acid-binding agent (e.g., a tertiary amine such as pyridine) is conveniently used. The acid-binding agent preferably is used in a large excess, so that it can simultaneously serve as the solvent. The subsequent cleavage of the tosylate preferably is carried out using lithium aluminium hydride in diethyl ether or tetrahydrofuran. The temperature and pressure for these reactions are not critical and atmospheric pressure and a temperature between about room temperature and about the reflux temperature preferably is used.

Under process (a), Compound Ia in which ring A is aromatic also can be reduced directly to Compound I by a Clemmensen reduction in a known manner. According to this reduction, ketone Ia is heated under reflux with amalgamated zinc and hydrochloric acid and, if necessary, with an inert organic solvent such as ethanol, acetic acid, dioxan, toluene and the like.

Furthermore, under process (a), Compound Ia in which ring A is aromatic can be reduced directly to Compound I by catalytic hydrogenation. This hydrogenation can be carried out with any conventional hydrogenation catalyst such as palladium platinum, Raney-nickel and the like. If desired, the catalytic hydrogenation can be supported on an inert carrier material. Palladium and platinum are the preferred catalysts. The solvent used can be any inert organic solvent such as a saturated alcohol, ether, ester, carboxylic acid and the like (e.g., ethanol, dioxan, ethyl acetate or glacial acetic acid). The temperature and pressure are not critical in this reaction. A temperature between about room temperature and about the boiling point of the mixture and a pressure of about 1 to about 5 atmospheres preferably are used.

Under process (a), Compound Ia in which $R^3$ is hydrogen, methyl, —CH$_2$R, —OR or —CH$_2$OR and R is as above are converted directly into the corresponding Compound I by the foregoing reduction. Compound Ia in which $R^3$ is —OR" or —CH$_2$OR" and R" is as above are further reacted to give alcohols as described earlier by cleavage of the alcohol protecting group denoted by R" and then esterifying the resulting hydroxy group to —O—CO—R or oxidizing the resulting hydroxymethyl group to the carboxyl group. If desired, the carboxyl group can be converted into —CO—OR, —CO—SR or —CN where R is as above by conventional techniques.

The above esterification of the resulting hydroxy group can be carried out by reacting the corresponding alcohol or a suitable salt thereof (e.g., the sodium salt) in a known manner with an alkanecarboxylic acid or a reactive derivative thereof (e.g., an anhydride or acid halide). The reaction of an alcohol with a carboxylic acid preferably is carried out in the presence of a catalytic amount of a strong acid (e.g., sulphuric acid or a hydrohalic acid) in the presence or absence of an inert organic solvent (e.g., benzene or toluene). It can, however, also be carried out in the presence of N,N'-dicyclohexylcarbodiimide and 4-(dimethylamino)pyridine. Preferably, the alcohol is reacted with an acid chloride (R—COCl wherein R is as above). This reaction preferably is carried out in an inert organic solvent, for example an ether (e.g., diethyl ether or tetrahydrofuran), dimethylformamide, benzene, toluene, cyclohexane, carbon tetrachloride and the like.

To bind the hydrogen chloride which is liberated during the above reaction, an acid-binding agent (e.g., tertiary amines, such as pyridine and the like) preferably is used. The acid-binding agent preferably is used in large excess, so that it can simultaneously serve as the solvent. The temperature and pressure are not critical and this reaction generally is carried out at atmospheric pressure and a temperature between about room temperature and about the boiling point of the reaction mixture.

Under process (a), oxidation of the resulting hydroxymethyl group to the carboxyl group can be carried out in a known manner. Illustratively, one can use silver oxide, chromium trioxide or a chromate oxidation agent, preferably Jones' reagent or pyridinium dichromate. The reaction can be carried out under any conventional conditions used in such oxidations.

The esterification of the resulting acid (Compound I in which $R^1$ is carboxyl and $R^2$ is alkyl) or a corresponding acid halide or anhydride (e.g., the acid chloride) with an alkanol or alkanethiol (ROH or RSH wherein R is as above) or a suitable salt thereof (e.g., the sodium salt, the potassium salt or the lithium salt) to give Compound I in which $R^1$ is —CO—OR or —CO—SR, R is as above and $R^2$ is alkyl can be carried out in an analogous manner to the esterification described earlier. The acid halides and anhydrides can be prepared in a known manner. For example, acid chlorides can be obtained by reacting the acid with phosphorus trichloride, phosphorus pentachloride, thionyl chloride and the like. The anhydrides are obtained by reacting the acid with acetic anhydride, acetyl chloride, ethyl chloroformate and the like. An especially preferred process for producing thioester Ia comprises reacting the corresponding acid with carbonyldiimidazole and subsequently esterifying with an alkanethiol. Methyl esters can also be obtained by reacting the corresponding carboxylic acid with diazomethane in an inert organic solvent, preferably diethyl ether.

Under process (a) the conversion of a resulting acid into the corresponding nitrile (Compound I in which $R^1$ is cyano and $R^2$ is alkyl) can be carried out in a known manner by converting the acid into the amide and subsequently dehydrating the amide.

The above amide preferably is prepared by firstly converting the acid into an acid halide or anhydride. It is preferred to react the acid with thionyl chloride phosphorus pentachloride, ethyl chloroformate and the like in an inert organic solvent (if desired, in the presence of a base such as triethylamine or pyridine) and subsequently to react the resulting acid chloride or mixed anhydride with ammonia to give the corresponding amide. The temperature and pressure are not critical in these reactions. Atmospheric pressure and a temperature between about 0° C. and about room temperature conveniently are used.

The dehydration of the above amide can be carried out using any conventional dehydrating agent such as, phosphorus oxychloride, phosphorus pentoxide, thionyl chloride, acetic anhydride or, especially, benzenesulphonyl chloride and the like. The dehydration can be carried out in an inert organic solvent such as a hydrocarbon or halogenated hydrocarbon (e.g., benzene, toluene or methylene chloride), if desired in the presence of a base such as sodium acetate, pyridine or triethylamine. It can, however, also be carried out in the absence of an organic solvent. If desired, the base, insofar as it is liquid at the reaction temperature, can also serve as the solvent. The reaction temperature preferably lies between about 50° C. and about the reflux temperature of the reaction mixture. The pressure is not critical and the reaction advantageously is carried out at atmospheric pressure.

In process (b), the reduction of Compound Ib and, if desired, the further conversion of the reduction product into Compound I in which $R^1$ is alkoxycarbonyl—CO—OR, alkylthiocarbonyl—CO—SR or cyano can be carried out by the methods of reduction, esterification and nitrile manufacture described above in process (a).

In the foregoing reductions, only the thioketal mthod and the catalytic hydrogenation lead directly to the corresponding Compound I for all groups denoted by $R^5$. In the case of reduction with hydrazine in the presence of a base (e.g., potassium hydroxide) or the Clemmensen reduction in the presence of an acid (i.e. hydrochloric acid), an ester group for $R^5$ (—CO—OR or —O—CO—R) can be saponified by conventional techniques. The resulting carboxyl or hydroxy group, if necessary, can be esterified again. Further, in the case of reduction with lithium aluminium hydride and the like, the $R^5$ groups are reduced to the hydroxymethyl or hydroxy group. If desired, these groups can also be converted into the —COOH, —CN, —CO—OR, —CO—SR or —O—CO—R where R is as above as described in process (a).

In process (c), the reduction of the tosylate of Compound II preferably is carried out by conventional techniques such as using lithium aluminium hydride in an inert organic solvent (e.g., an ether such as diethyl ether, tetrahydrofuran and the like). The temperature and pressure of the reaction are not critical. Atmospheric pressure and a temperature between about room temperature and about reflux temperature preferably are used. By process (a), one can prepare the tosylate from alcohol II. In an analogous manner to that described in process (a), one can cleave alcohol protecting group R'', if present, esterify the resulting hydroxy group to —O—CO—R, or oxidize the resulting hydroxymethyl group to the carboxyl group. If desired, one can further convert the carboxyl group into —CO—OR, —CO—SR or —CN, where R is as above in a manner analogous to that described in process (a).

In process (d), the etherification of Compound III conveniently is carried out by reacting a corresponding alcoholate (e.g., sodium alcoholate) with a corresponding alkyl halide, preferably the alkyl bromide or alkyl iodide (R'Br or R'I wherein R' is as above). The alcoholate can be obtained in a known manner. For example, one can react the alcohol with an alkali metal or alkali metal hydride (e.g., sodium, sodium hydride or potassium hydride). The etherification conveniently is carried out in an inert organic solvent (e.g., a hydrocarbon, an ether, acetone or dimethylformamide). A preferred embodiment of this process for Compound III in which ring A is saturated, comprises reacting alcohol with sodium hydride or potassium hydride and an alkyl bromide or iodide (R'Br or R'I wherein R' is as above) in dimethyl-formamide or tetrahydrofuran/dimethylformamide (4:1 parts by volume) at about 0° C. to about room temperature.

A preferred embodiment of this process for Compound III in which ring A is aromatic comprises reacting the alcohol with the alkyl bromide or iodide in the presence of a suitable weak base such as an alkali metal carbonate (e.g., potassium carbonate) in acetone at a temperature between about room temperature and about reflux temperature, preferably at about the reflux temperature. The temperature and pressure are not critical. The reaction, however, preferably is carried out at atmospheric pressure and about room temperature. The cleavage of an alcohol protecting group R'', if present, and the further conversion into one of the groups —O—CO—R, —COOH, —CO—OR, —CO—SR or —CN where R is as above can be carried out as described in process (a).

In process (e), the reaction of Compound IVa with a carboxylic acid chloride, bromide or anhydride, preferably an acid chloride (R'COCl wherein R' is as above), in the presence of a Lewis acid (e.g., aluminium trichloride, tin tetrachloride, boron trifluoride and the like, preferably aluminium trichloride) can be carried out by the conventional methods of Friedel-Crafts acylation. Illustratively, the reaction is carried out in an inert organic solvent (e.g., carbon disulphide or a chlorinated hydrocarbon, preferably methylene chloride or chloroform). The reaction temperature conveniently lies between about 0° C. and about the reflux temperature of the reaction mixture. The pressure is not critical. The reaction advantageously is carried out at atmospheric pressure and about room temperature. if desired, Compound I in which $R^1$ is —CO—OR can be hydrolyzed to the corresponding carboxylic acid in a known manner with an acid or a base such as sulphuric acid, hydrochloric acid, sodium hydroxide, potassium hydroxide and the like. If desired, the carboxyl group then can be converted into —CO—SR or —CN where R is as above as described in process (a).

In process (f), the oxidation of Compound Va can be carried out in a known manner. For example, one can use chromic acid in acetone, sodium dichromate or chromium trioxide in sulphuric acid, chromium trioxide in pyridine, pyridinium chlorochromate, pyridinium dichromate, acetic anhydride and dimethyl sulphoxide, dicyclohexylcarbodiimide and dimethyl sulphoxide in phosphoric acid and the like.

In this oxidation, the temperature and pressure are not critical. The configuration of the cyclohexane ring is largely preserved in this oxidation (i.e., when one uses Compound Va with a trans-1,4-disubstituted cyclohexane ring, then the subsequent reaction with a strong base can be omitted). It, however, is preferred firstly to oxidize a cis/trans mixture of Compound Va and subsequently to convert the product under basic conditions into a cis/trans equilibrium mixture. The amount of trans compound present in such an equilibrium mixture is generally greater than about 90%. This equilibration is conveniently carried out in an inert organic solvent, for example with an alkali metal hydroxide in an alcohol (e.g., methanol or ethanol) and preferably with methanolic potassium hydroxide solution or ethanolic sodium hydroxide solution. Temperature and pressure are not critical and the reaction advantageously is carried out at atmospheric pressure and about room temperature. If the equilibration is carried out with a base, ester —O—CO—R or —CO—OR which may be present, however, is saponified to the hydroxy or carboxyl group. As described in process (a), the hydroxy group is therefore esterified again and the carboxyl group, if desired, is converted into —CO—OR, —CO—SR or —CN wherein R is as above.

In process (g), the dehydration of Compound VIa in which $R^9$ is —CONH$_2$ can be carried out in an analogous manner to the dehydration of an amide as described under process (a). Under process (g), the dehydration of Compound VIa in which $R^9$ is —CH=N—OH, conveniently is carried out using acetic anhydride or using anhydrous sodium acetate in glacial acetic acid. The reaction temperature is about reflux temperature of the reaction mixture. The pressure is not critical and the reaction is advantageously carried out at atmospheric pressure.

In process (h), the reaction of Compound VIIa with copper (I) cyanide, sodium cyanide or potassium cyanide conveniently is carried out in an inert organic solvent such as ethyleneglycol, tetrahydrofuran, dimethylformamide, dimethyl sulphoxide, pyridine or acetonitrile. Reaction with copper (I) cyanide in dimethylformamide is preferred. The temperature and pressure are not critical in this reaction. Atmospheric pressure and a temperature between about room temperature and about boiling point of the reaction mixture conveniently are used.

In process (i), the oxidation of Compound Ic can be carried out in a known manner. The oxidation of a methyl ketone (i.e., Compound Ic in which $R^{10}$ is methyl), conveniently is carried out using a hypohalite, preferably an alkali metal hypochlorite or hypobromite such as sodium hypobromite, sodium hypochlorite, potassium hypobromite and the like in an inert organic solvent (e.g., dioxan or tetrahydrofuran). Preferred oxidizing agents for the oxidation of an aldehyde (i.e., Compound Ic in which $R^{10}$ is hydrogen), are potassium permanganate, chromic acid and the like. The temperature and pressure are not critical. Atmospheric pressure and a temperature between about room temperature and about 50° C. preferably are used.

In process (j), the esterification of Compound Id or a reactive derivative, preferably the acid chloride, with an alkanol, an alkanethiol or a suitable salt thereof (R'OH or R'SH wherein R' is as above or e.g. the sodium salt thereof) can be carried out in an analogous manner to the esterification described earlier under process (a) of Compound I in which $R^1$ is carboxyl and $R^2$ is alkyl.

In process (k), the conversaion of Compound Ie into the corresponding ester can be carried out according to the methods of the known Baeyer-Villiger reaction with a peracid such as Caro's acid, perbenzoic acid, monoperphthalic acid, peracetic acid, trifluoroperacetic acid and preferably 3-chloroperbenzoic acid. The reaction conveniently is carried out in an inert organic solvent, preferably a chlorinated hydrocarbon such as methylene chloride, chloroform and the like and with the exclusion of light. The reaction preferably occurs at about room temperature and atmospheric pressure. The duration of the reaction generally is about 2 to 3 days. Since the oxygen atom is introduced predominantly on the side of the higher substituted carbon atom (adjacent to the carbonyl group) with retention of the configuration, the reaction primarily is suitable for manufacturing Compound I in which $R^2$ is alkanoyloxy —O—CO—R' and R' is methyl or primary alkyl.

In process (l), the esterification of Compound IIIa or a suitable salt thereof (e.g., the sodium salt or the potassium salt) can be carried out according to the methods for esterifying a hydroxy group described under process (a). This process is suitable for manufacturing all compounds of formula I in which $R^2$ is alkanoyloxy —O—CO—R' and R' is alkyl. It is especially suitable for those compounds in which R' in the alkanoyloxy group is a secondary or tertiary alkyl because one obtains better yields and less purification problems than if the Baeyer-Villiger process were utilized. Starting Compound IIIa conveniently is prepared from Compound Ie in which R' is methyl or primary alkyl by a conventional Baeyer-Villiger reaction and by subsequent hydrolysis of the resulting ester.

In process (m), the esterification of Compound VLII or a suitable salt thereof (e.g., the sodium salt) also can be carried out according to the methods for esterifying a hydroxy group as described under process (a).

In process (n), the etherification of Compound VLII can be carried out in an analogous manner to that described in process (d) by reacting a corresponding alcoholate (e.g. the sodium or potassium alcoholate) with an alkyl halide (e.g. the alkyl bromide or iodide).

The configuration of the decalin structure is not changed by all the foregoing reactions. By using the corresponding starting materials there can be manufactured not only Compounds IA and IB but also mixtures of the two.

Compounds Ia-Ie which do not fall under formula I as well as Compounds II, III, IIIa, IVa, VIa and VIIa are novel and also form objects of the present invention. The preparation of these starting materials and examples for the manufacture of Compound I are illustrated by the following Reaction Schemes 1-7 in which A, R, R', R'', $R^3$, $R^4$ and $X^1$ are as above, $R^{11}$ is hydrogen, methyl, —CH$_2$R, —OR, —OR'', —CH$_2$OR, —CH$_2$OR'', —CO—OR or —O—CO—R, $R^{12}$ is one of the values accorded to $R^{11}$ or carboxyl, X is oxygen or sulphur, Ts is p-tosyl and the symbol ⌇ indicates that the bond in question can lie below or above the plane of the drawing, i.e., the cyano group (in Schemes 1 and 3) can have the α- or β-configuration or the cyclohexane ring (in Scheme 4) can be trans- or cis-disubstituted.

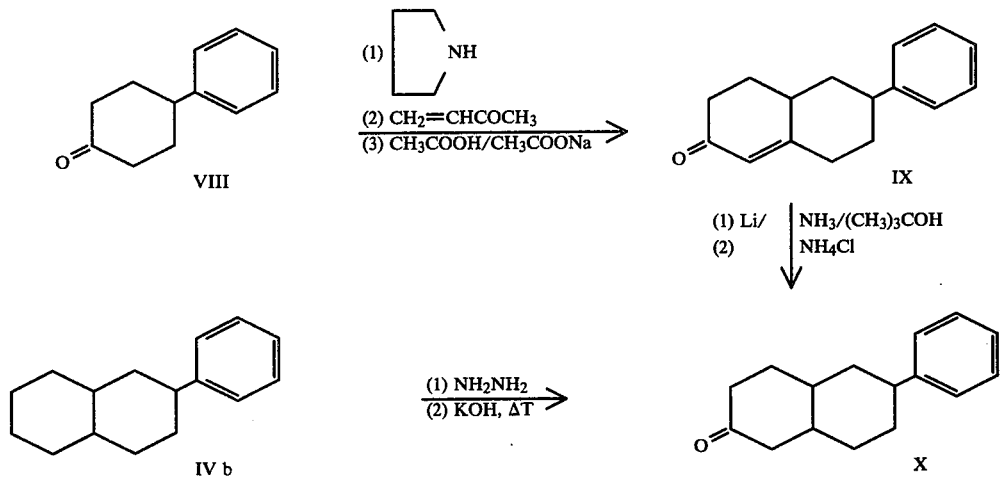

Scheme 1

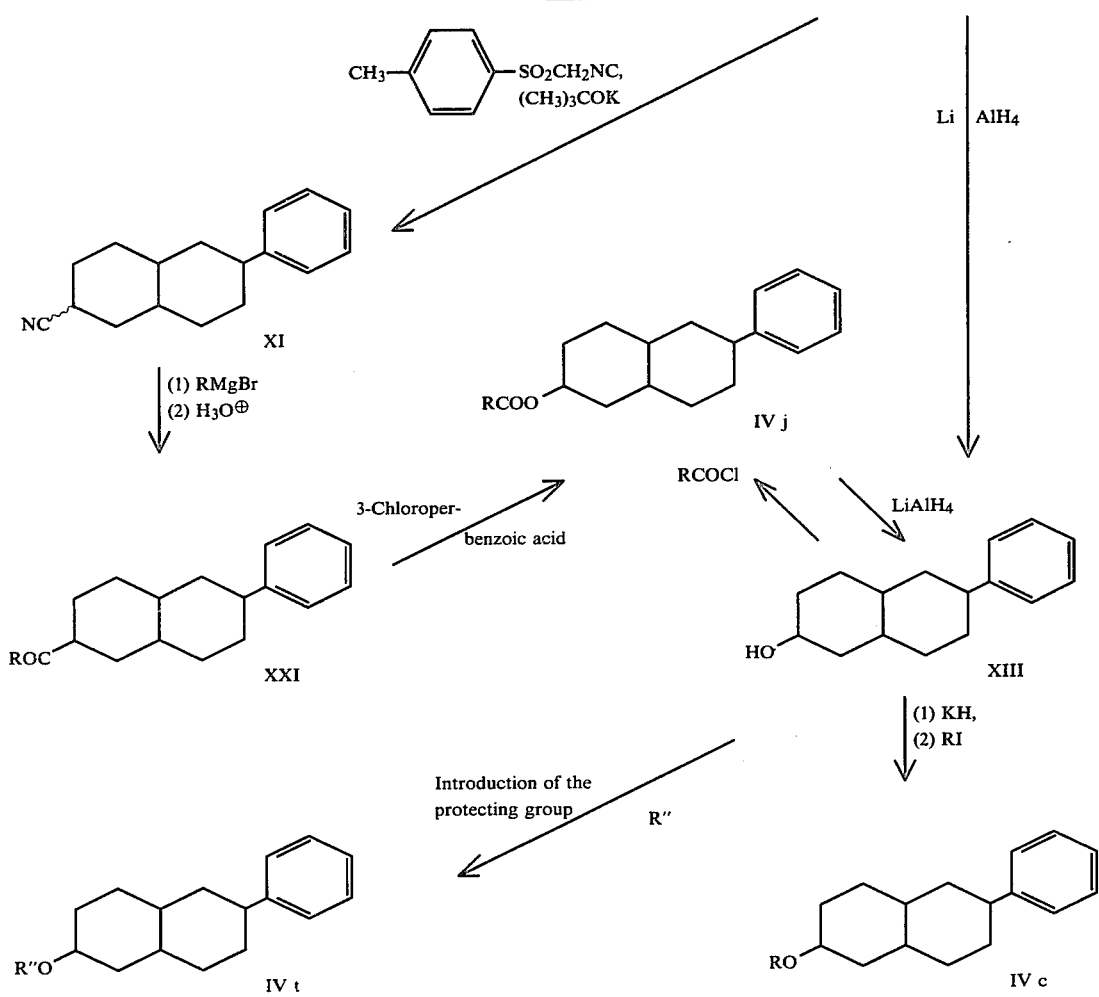
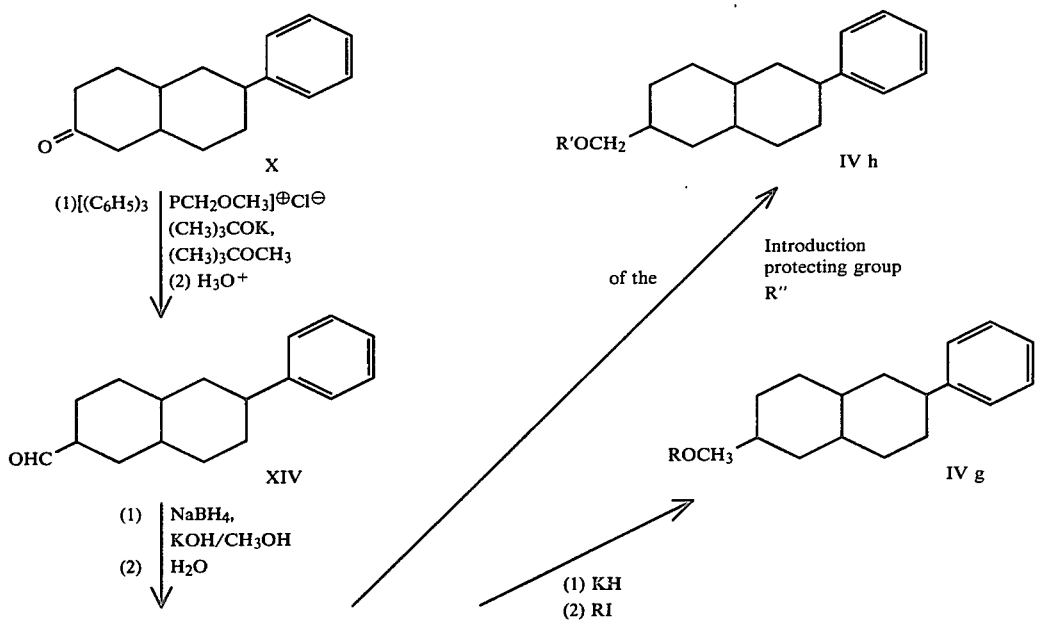

-continued
Scheme 2
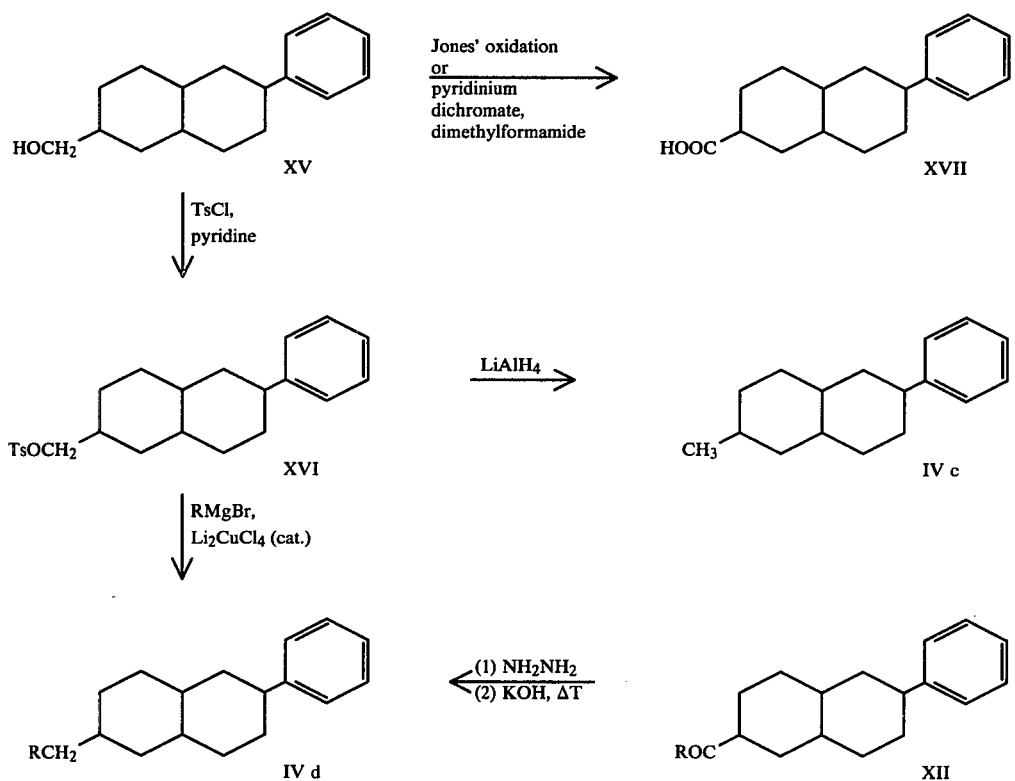
Scheme 3
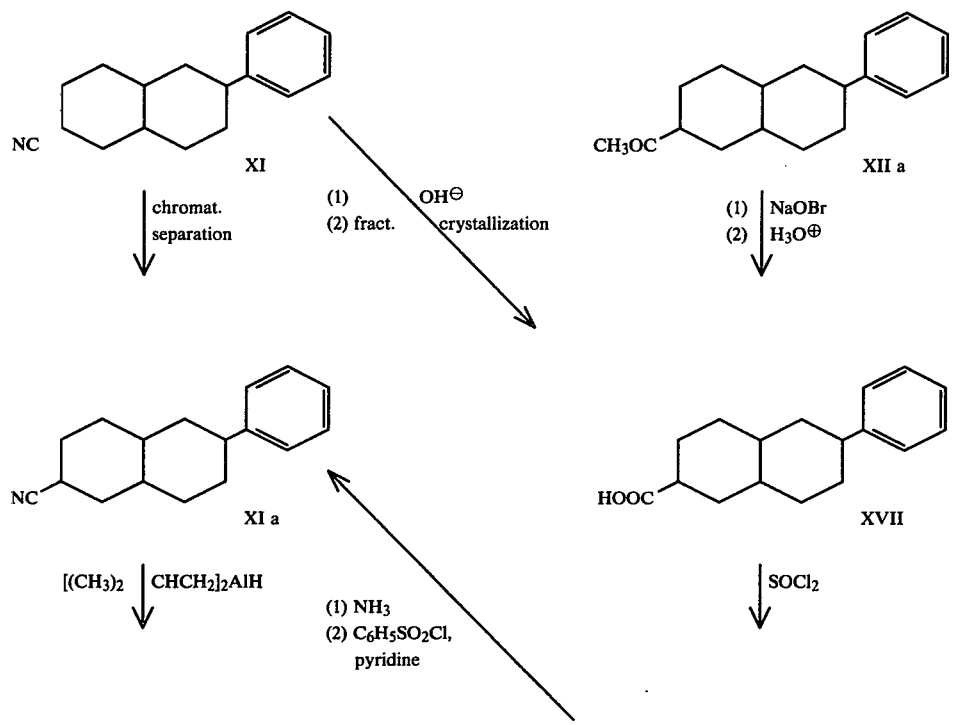

-continued
Scheme 3
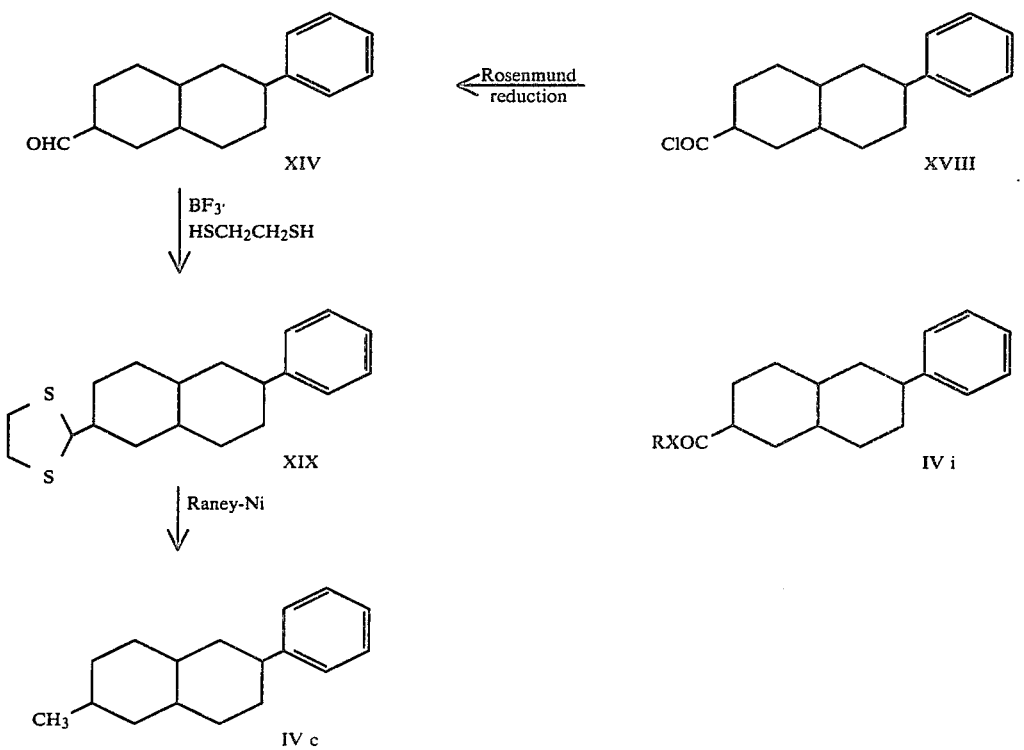
Scheme 4
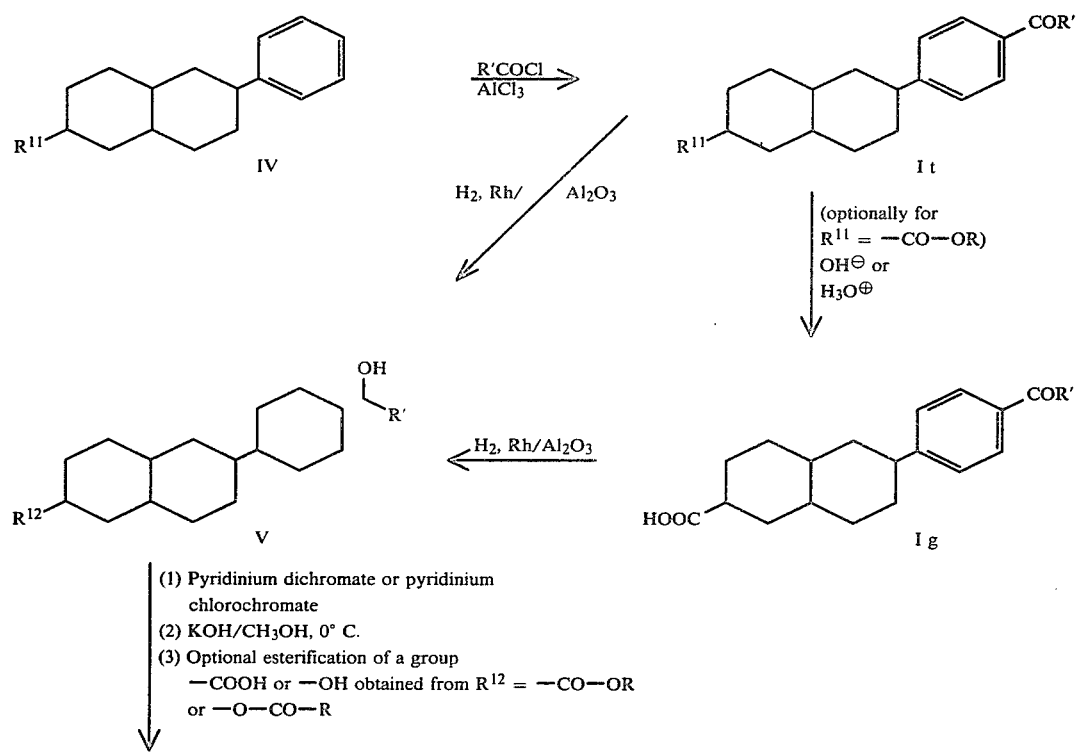

4,432,885
-continued
Scheme 4
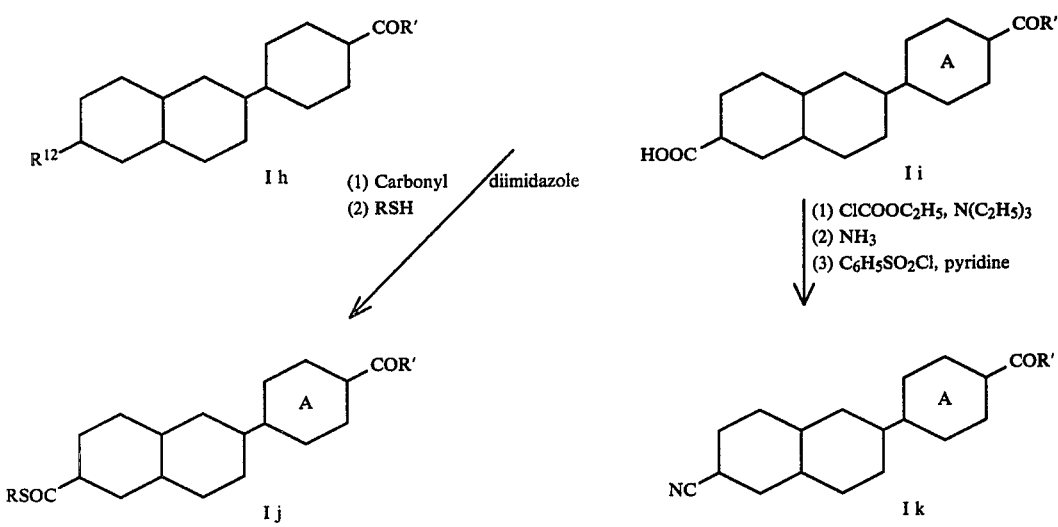
Scheme 5
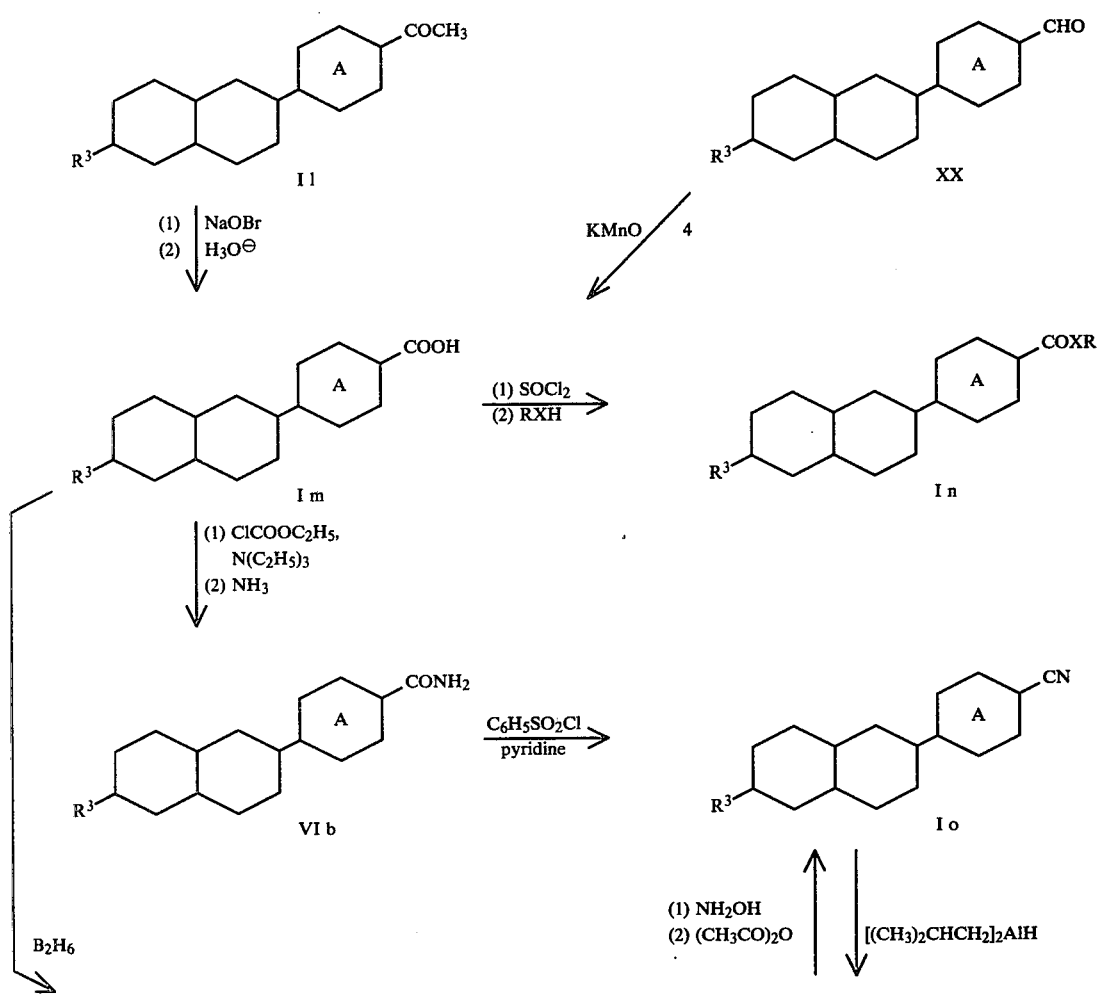

-continued
Scheme 5
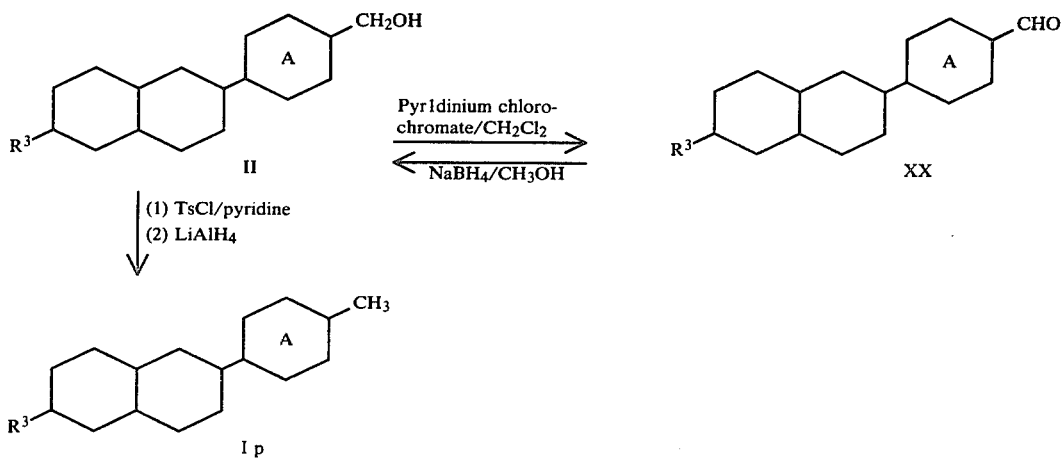
Scheme 6
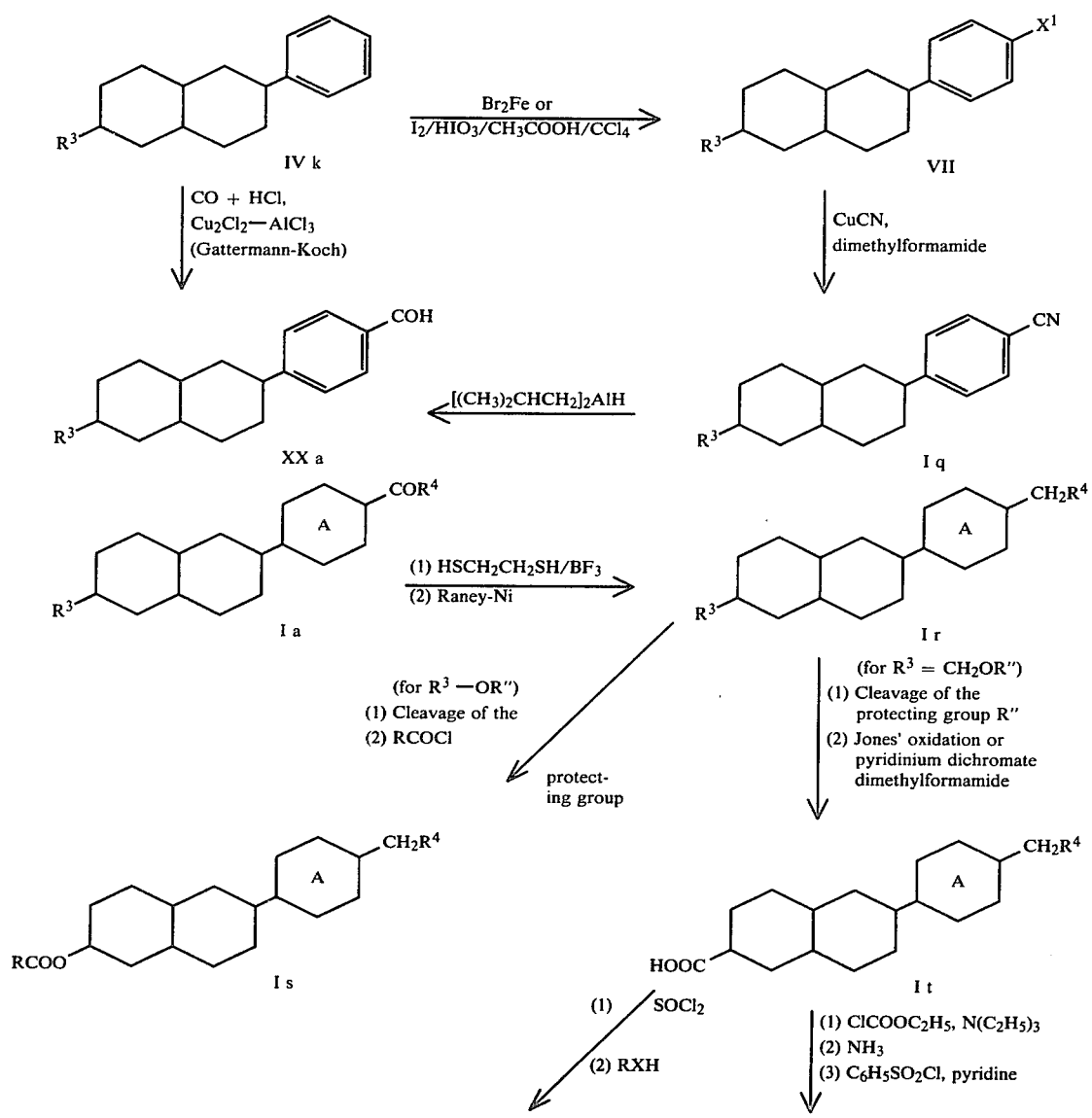

-continued
Scheme 6

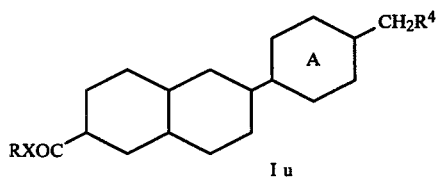
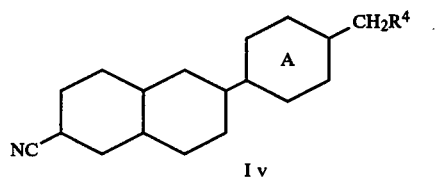

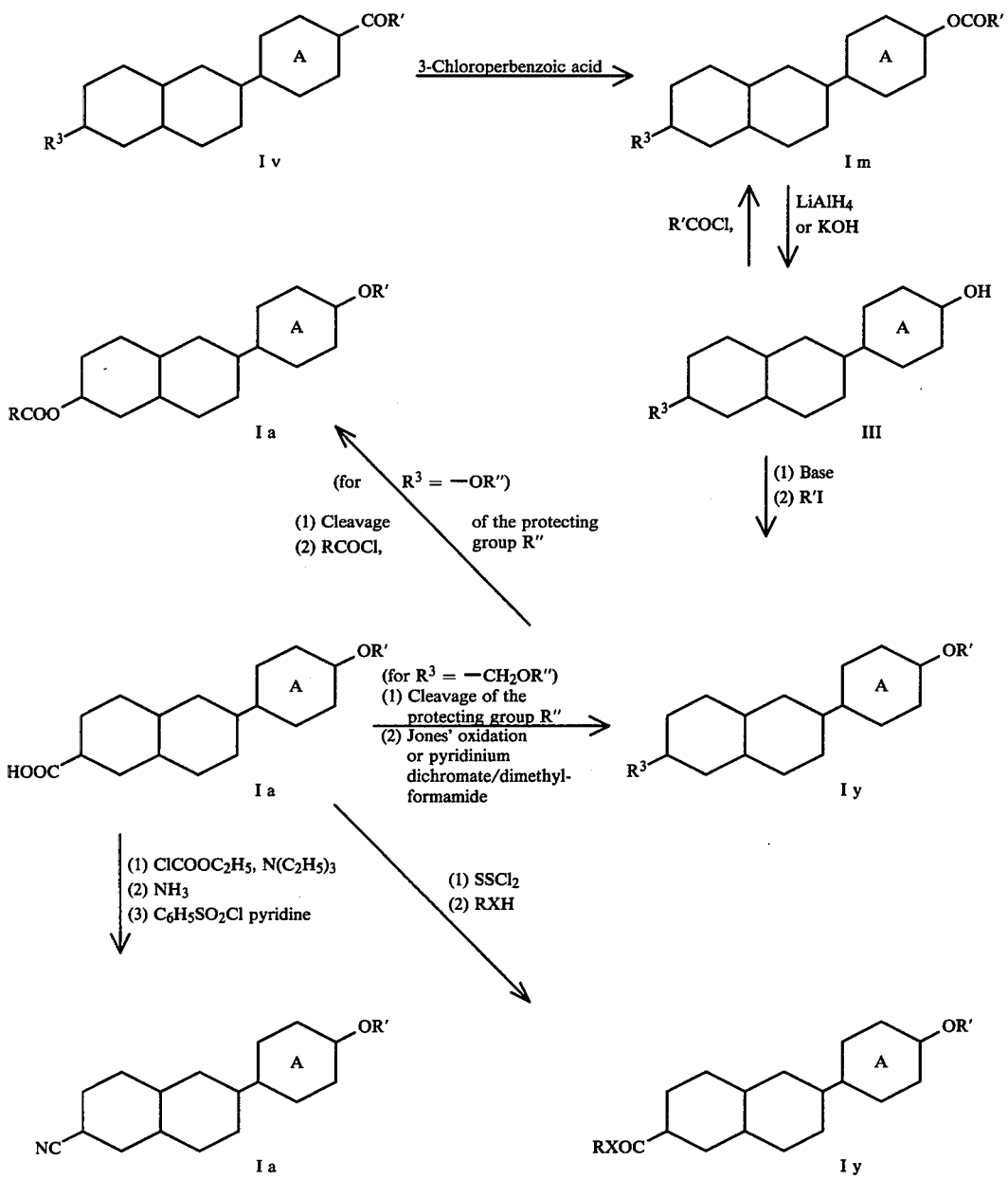

The diastereomeric mixture of Compound XI can be separated by conventional chromatographic techniques. However, conversion into acid XVII, separation by fractional crystallization and conversion into nitrile XIa is more suitable. On the other hand, if nitrile XI is to be converted into Compound XII, then the separation advantageously is carried out only after a Grignard reaction and a subsequent equilibrating hydrolysis by crystallization of Compound XII.

The introduction and cleavage of alcohol protecting group R" (in Schemes 1, 2, 6 and 7) can be carried out as described earlier.

Illustratively, acid XVII also can be obtained from aldehyde XIV by oxidation with potassium permanganate.

If desired, the racemate of acid XVII can be resolved into its optical antipodes by conventional resolving techniques. In so doing, acid XVII conveniently is reacted with an optically active base such as optically active phenylethylamine, ephedrine, cinchonidine, naphthylethylamine, methylbenzylamine and the like. The resulting mixture of diastereomeric salts then is separated by crystallization and the resulting optically active salt is hydrolyzed. Thus, all compounds of formula IA or IB can be obtained starting from an optically active acid of formula XVII.

Compound VLII is novel and likewise forms an object of the present invention.

For the preparation of Compound VLII, a compound of formula IVj (Scheme 1) can be acylated in the p-position of the phenyl ring according to the Friedel-Crafts process (e.g., using aluminium chloride and an alkanoyl chloride). Subsequently, the keto group can be reduced to the methylene group by catalytic hydrogenation with palladium/carbon. The ester group then can be saponified or the keto ester can be converted according to the Baeyer-Villiger process (e.g., using m-chloroperbenzoic acid) into a diester. This diester then can be converted (e.g., using lithium aluminium hydride) into the dihydroxy compound and the phenolic hydroxy group can be etherified in acetone using an alkyl iodide and potassium carbonate.

Compound VLII in which $R^{26}$ is methyl or $-CH_2R'$ and $R'$ is as above, however, can be prepared in a simpler manner. In particular one acylates Compound X in the p-position of the phenyl ring according to the Friedel-Crafts or the Gattermann-Koch process, then reduces the carbonyl group on the phenyl ring to the methylene group by catalytic hydrogenation with palladium/carbon and finally reduces the 2-oxo-group (on the decalin structure) to the hydroxy group using lithium aluminium hydride.

The present invention also concerns liquid crystalline mixtures.

The compounds of formula I are valuable especially as components of liquid crystalline mixtures. Most of such compounds exhibit liquid crystalline properties. More particularly, the optically active forms of the compounds generally exhibit a cholesteric-type mesophase and the optically inactive compounds (racemates) generally exhibit a nematic mesophase. The inventive compounds preferably are used for manufacturing nematic and cholesteric-type liquid crystalline mixtures having positive anisotropy of the dielectric constants.

The compounds of formula I can be mixed with other liquid crystalline and/or non-liquid crystalline substances to form liquid crystalline mixtures. Illustratively, such substances can be selected from classes of Schiff's bases, azobenzenes, azoxybenzenes, phenyl benzoates, cyclohexanecarboxylic acid phenyl esters, biphenyls, terphenyl, phenylcyclohexanes, cinnamic acid derivatives, phenyl pyrimidines, diphenylpyrimidines, phenyldioxanes, cyclohexylphenylpyrimidines and the like. Such substances are known to a person skilled in the art. See, e.g., German Offenlegungsschriften Nos. 2,306,738 (U.S. Pat. No. 3,927,064); 2,306,739 (U.S. Pat. No. 3,923,857); 2,429,093; 2,356,085 (U.S. Pat. No. 3,947,375); 2,636,684 (U.S. Pat. No. 4,130,502); 2,459,374 (U.S. Pat. No. 3,927,066); 2,547,737 (U.S. Pat. No. 3,997,536); 2,641,724 (U.S. Pat. No. 4,062,798); 2,708,276 (U.S. Pat. No. 4,180,475); and 2,811,001 (U.S. Pat. No. 4,309,539); East German Patent Specifications Nos. 139,852 and 139,867 and from European Patent Application Publication Number 0014885 (U.S. Pat. No. 4,273,929). Many of such substances are available commercially. The inventive compounds can also be used as mixtures which consist only of two or more compounds of formula I.

The inventive mixtures also can contain hydrogenated naphthalenes of the formula

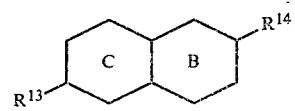

XXI wherein ring B is saturated or aromatic with the saturated ring B being trans-linked with C; $R^{13}$ is straight-chain alkyl or alkoxy of 1 to 11 carbon atoms; $R^{14}$ is cyano, straight-chain alkyl of 1 to 11 carbon atoms or an ester group of the formula

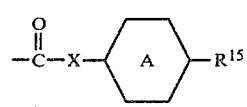

XXII or, when ring B is saturated, $R^{14}$ can also be straight-chain alkoxy of 1 to 11 carbon atoms; in ester XXII ring A is aromatic, X is oxygen or sulphur and $R^{15}$ is cyano or straight-chain alkyl or alkoxy of 1 to 10 carbon atoms, or ring A is a trans-1,4-disubstituted cyclohexane ring, X is oxygen and $R^{15}$ is cyano or straight-chain alkyl of 1 to 10 carbon atoms; with the proviso that the total number of carbon atoms in the alkyl and alkoxy groups present is at most 12;
and/or benzodioxanes of the formula

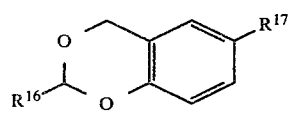

XXIII wherein $R^{16}$ is straight-chain alkyl of 1 to 11 carbon atoms; $R^{17}$ is cyano, straight-chain alkyl of 1 to 11 carbon atoms or ester XXII hereinbefore in which X, A and $R^{15}$ are as above; with the proviso that the total number of carbon atoms in the alkyl and alkoxy groups present is at most 12,
and/or trans-(4-alkylcyclohexyl)pyrimidines of the formula

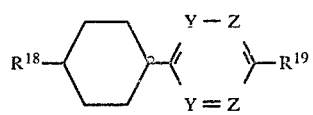

XXIV wherein Y is nitrogen and Z is =CH—, or Z is nitrogen and Y is =CH—; $R^{18}$ is alkyl and $R^{19}$ is cyano, alkyl, p-alkylphenyl or trans-4-alkylcyclohexyl; where each alkyl denotes either a straight-chain alkyl group of 1 to 12 carbon atoms or a branched-chain alkyl group of the formula $C_2H_5-CH(CH_3)-(CH_2)_n$, n is 1, 2 or 3; with the proviso that the compound contains at most only one of said branched-chain alkyl group and with the further proviso that the sum of the carbon atoms in all of the alkyl groups within the compound is at most 14.

Compounds XXI, XXIII and XXIV are novel. Compound XXI in which $R^{14}$ is cyano, straight-chain alkyl or straight-chain alkoxy and Compound XXIII in which $R^{17}$ is cyano or straight-chain alkyl are above all suitable as doping agents in liquid crystal mixtures and in general are not liquid crystalline themselves. In mixtures which contain such doping agents, at least one compound with liquid crystalline properties must be present in sufficient amount so that the total mixture also has liquid crystalline properties. The remaining compounds of formulae XXI and XXIII as well as the compounds of formula XXIV are, on the other hand, to a large extent themselves liquid crystalline.

In accordance with the present invention, Compound XXI can be manufactured as follows:

(o) for Compound XXI in which $R^{14}$ is ester XXII, esterifying a compound of the formula

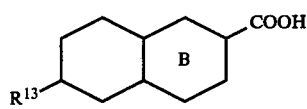   XXVI wherein $R^{13}$ and ring B are as above,
or a reactive derivative thereof, (e.g., the corresponding acid chloride) with a compound of the formula

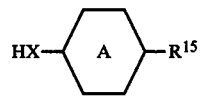   XXV wherein X, ring A and $R^{15}$ are as above;

(p) for Compound XXI in which $R^{14}$ is cyano, dehydrating a compound of the formula

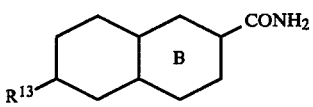   XXVII wherein $R^{13}$ and ring B are as above;

(q) for Compound XXI in which $R^{14}$ is straight-chain alkyl, reacting a compound of the formula

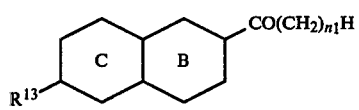   XXVIII wherein $n_1$ is an integer of 0 to 10 and $R^{13}$, ring B and ring C are as above,
with hydrazine in the presence of a base;

(r) for Compound XXI in which ring B is saturated and $R^{14}$ is straight-chain alkoxy, etherifying a compound of the formula

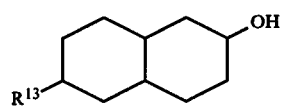   XXIX wherein $R^{13}$ is as above.

Compound XXV is known or can be made from known compounds by conventional techniques. The preparation of the Compounds XXVI–XXIX is illustrated by the following Reaction Schemes A–C in which $R^{13}$, B and $n_1$ are as above, $n_2$ is an integer of 1 to 10, the symbol (∼) indicates that the substituent in question can have the α- or β-configuration (below or above the plane of the formula) and the dotted line (---) indicates that one of the bonds denoted thereby is a double bond.

Scheme A

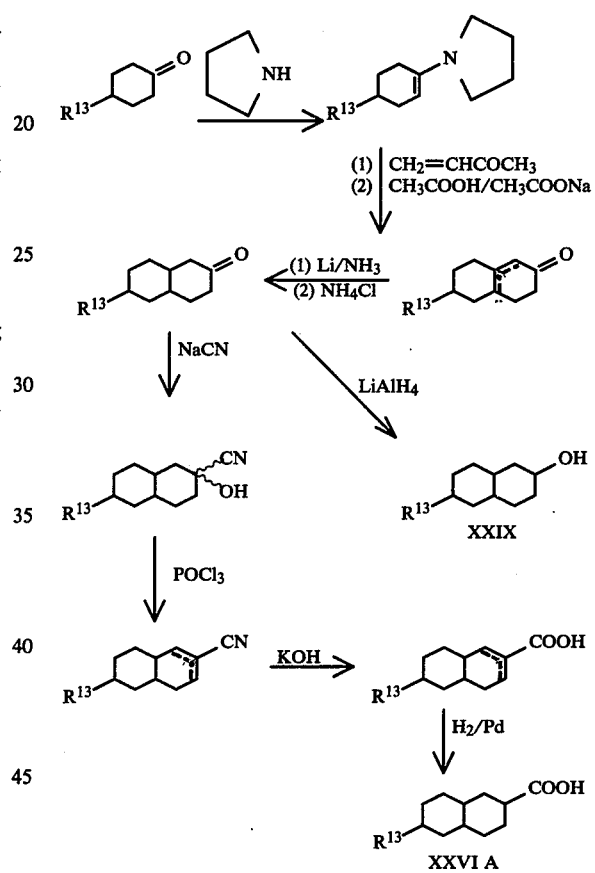

Scheme B

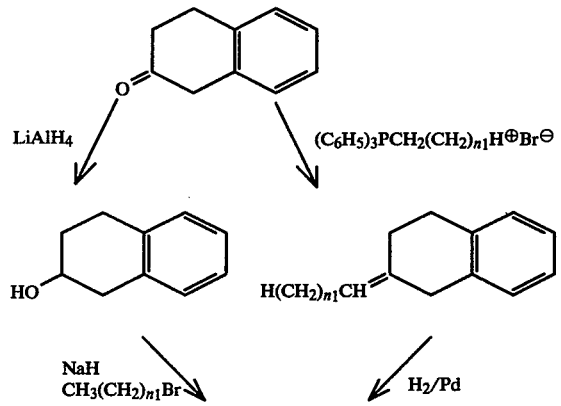

Scheme B

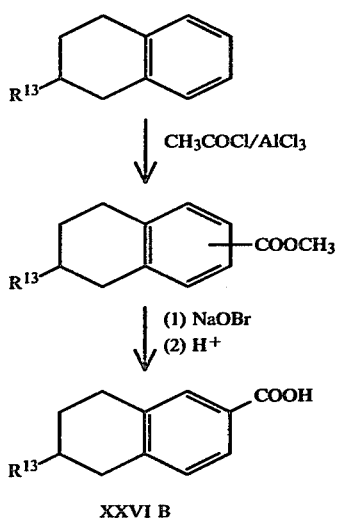

Scheme C

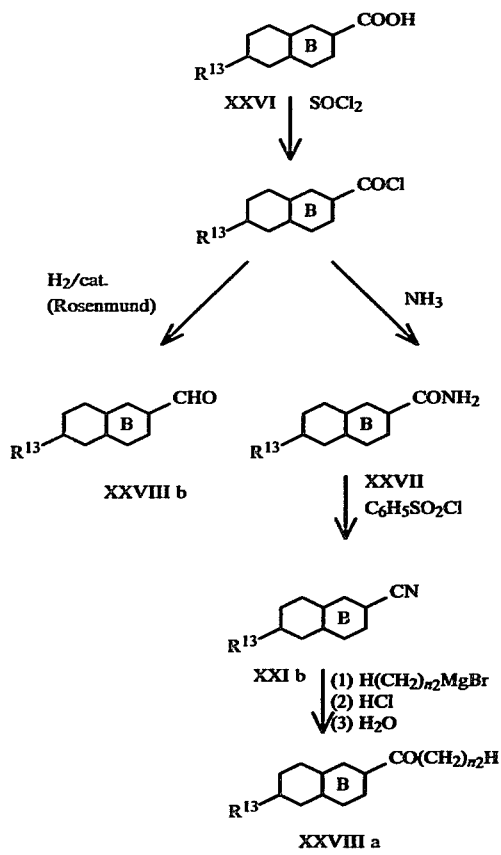

In accordance with the invention, Compound XXIII can be manufactured as follows:

(s) for Compound XXIII in which $R^{17}$ is ester XXII, esterifying a compound of the formula

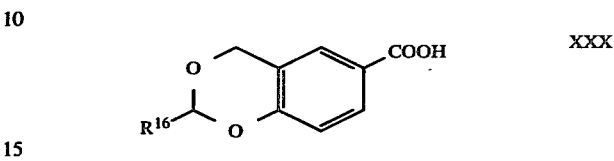

wherein $R^{16}$ is as above, with Compound XXV;

(t) for Compound XXIII in which $R^{17}$ is cyano, dehydrating a compound of the formula

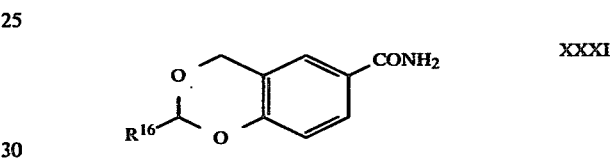

wherein $R^{16}$ is as above;

(u) for Compound XXIII in which $R^{17}$ is straight-chain alkyl of 2 to 11 carbon atoms, catalytically hydrogenating a compound of the formula

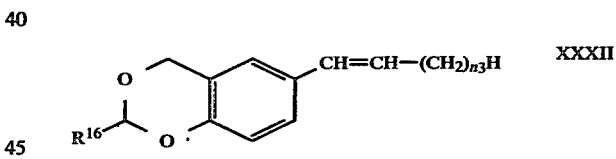

wherein $n_3$ is an integer of 0 to 9 and $R^{16}$ is as above;

(v) for Compound XXIII in which $R^{17}$ is methyl, reacting a compound of the formula

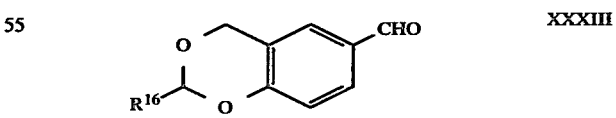

wherein $R^{16}$ is as above, with hydrazine in the presence of a base.

Compounds XXX–XXXIII used as the starting materials can be prepared according to the following Scheme D in which $R^{16}$ and $n_3$ are as above.

Scheme D

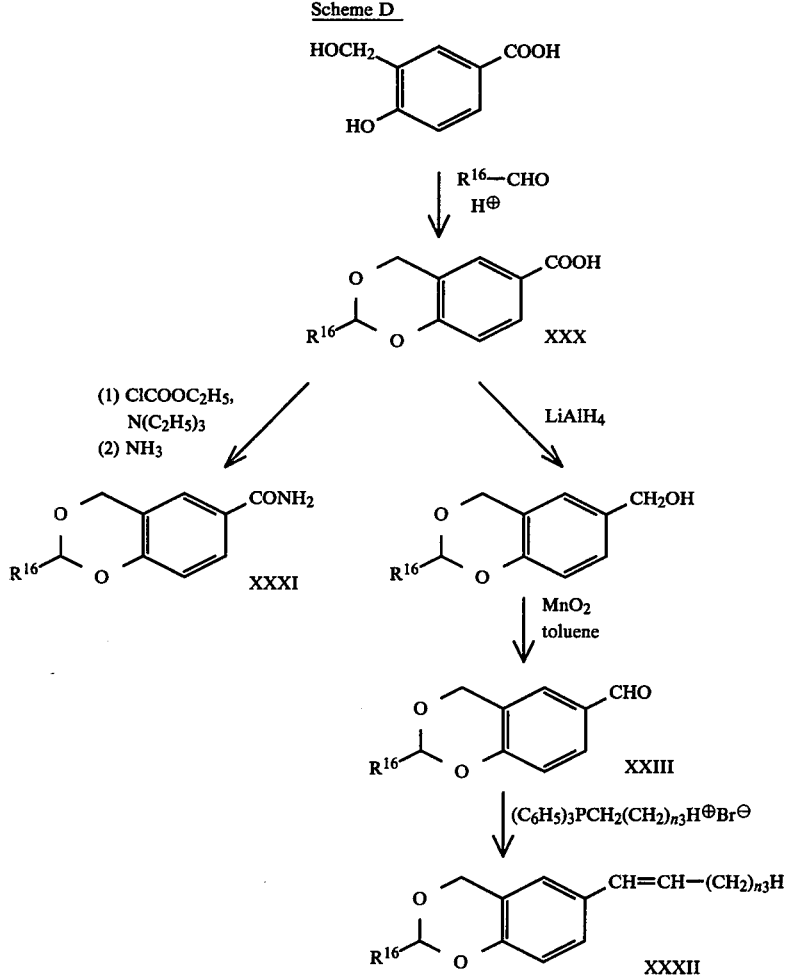

In accordance with the invention, Compound XXIV can be manufactured as follows:

(w) for Compound XXIV in which $R^{19}$ is alkyl, p-alkylphenyl or trans-4-alkylcyclohexyl, reacting a compound of the formula

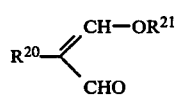 XXXIV with an acid addition salt (preferably the hydrochloride) of a compound of the formula

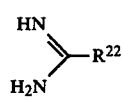 XXXV wherein one of $R^{20}$ and $R^{22}$ is trans-4-alkylcyclohexyl and the other is alkyl, p-alkylphenyl or trans-4-alkylcyclohexyl and $R^{21}$ is lower alkyl, in the presence of a base (preferably an alcoholate);

(x) for Compound XXIV in which $R^{19}$ is cyano, dehydrating a compound of the formula

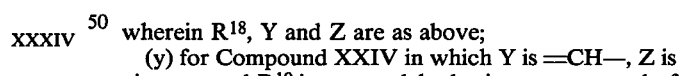 XXXVI wherein $R^{18}$, Y and Z are as above;

(y) for Compound XXIV in which Y is =CH—, Z is nitrogen and $R^{19}$ is cyano, dehydrating a compound of the formula

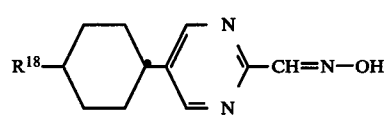 XXXVII wherein $R^{18}$ is as above.

Compounds XXXIV and XXXV are known compounds or can be produced from known compounds by known methods. [Z. Naturforsch. 33 b, 433 (1978) and 34 b, 1535 (1979)].

The preparation of the starting materials of formulae XXXVI and XXXVII is illustrated by the following Reaction Schemes E and F in which $R^{18}$ is as above.

Scheme E
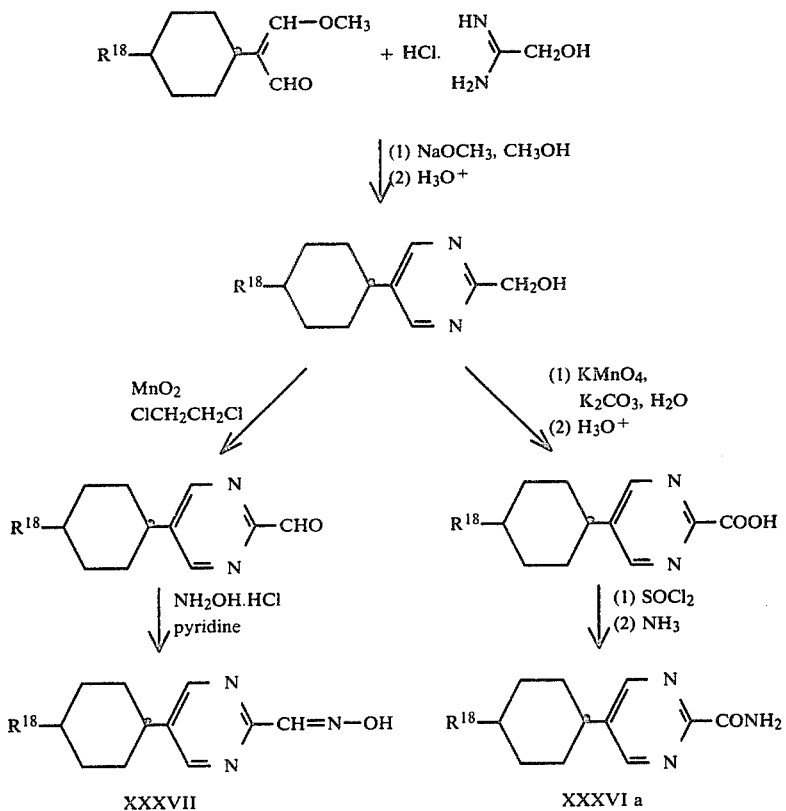
Scheme F
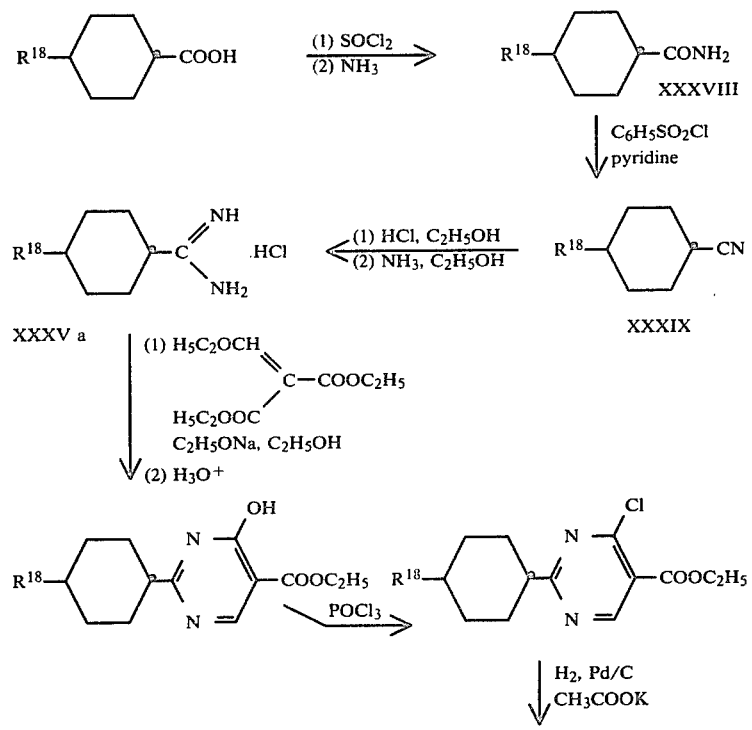

Scheme F

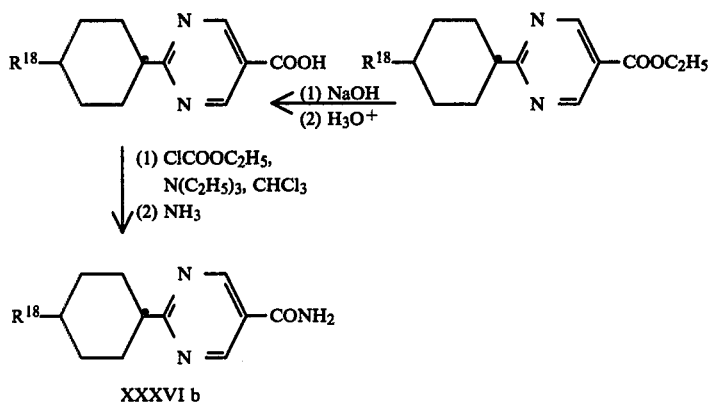

XXXVI b

The starting materials used in Schemes E and F are known or can be made from known compounds by conventional techniques. Illustratively, such compounds or analogs of these compounds are described, for example, in Z. Naturforsch. 34 b, 1535 (1979) and in Mol. Cryst. Liq. Cryst. 37, 189 (1976) or 42, 215 (1977).

In addition to one or more of Compound I, the inventive liquid crystal mixtures preferably can include one or more of the following compounds: 4-Cyanobiphenyls of the formula

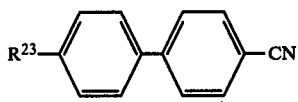

XL wherein $R^{23}$ is straight-chain alkyl or alkoxy of 2 to 7 carbon atoms; trans-p-(4-alkylcyclohexyl)benzonitriles of the formula

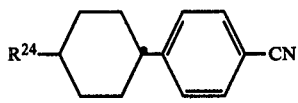

XLI wherein $R^{24}$ is straight-chain alkyl of 3 to 7 carbon atoms; p-(5-alkyl-2-pyrimidinyl)benzonitriles of the formula

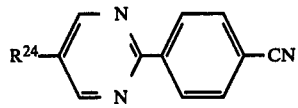

XLII wherein $R^{24}$ is as above; p-(trans-5-alkyl-m-dioxan-2-yl)benzonitriles of the formula

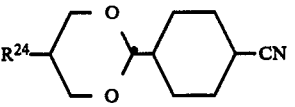

XLIII wherein $R^{24}$ is as above; p-alkylbenzoic acid p'-cyanophenyl esters of the formula

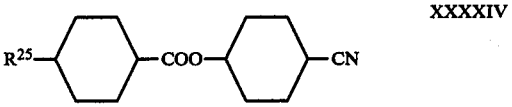

XXXXIV wherein $R^{25}$ is straight-chain alkyl of 2 to 7 carbon atoms, trans-4-alkylcyclohexanecarboxylic acid phenyl esters of the formula

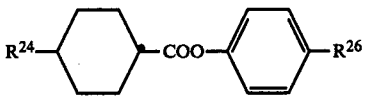

VL wherein $R^{24}$ is as above and $R^{26}$ is cyano or straight-chain alkoxy of 1 to 3 carbon atoms; trans-p-[5-(4-alkylcyclohexyl)-2-pyrimidinyl]-benzonitriles of the formula

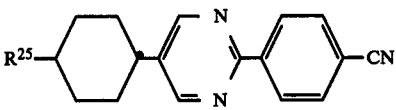

VLI wherein $R^{25}$ is as above; and/or p-[2-(trans-4-alkylcyclohexyl)-1-ethyl]benzonitriles of the formula

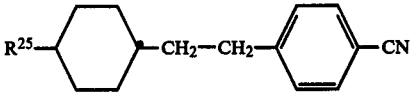

VLIII wherein $R^{25}$ is as above.

The weight ratio of the components of the inventive mixture preferably corresponds to the eutectic composition. In accordance with the invention, the mixtures can include two or more compounds of formula I (or at least one compound of formula I) and one or more other liquid crystalline or non-liquid crystalline substances. The amount of Compound I in the inventive liquid crystal mixtures is, however, preferably about 1 to about 80 mol percent, more particularly about 5 to about 60 mol percent. In mixtures including Compound I in which $R^1$ is alkyl and $R^2$ is alkanoyl, the amount of the compounds having an aromatic ring A, however, is from about 0 and generally up to about 50 mol percent and amount of the compounds having a saturated ring A is from 0 and generally up to about 30 percent.

The inventive liquid crystalline mixtures can contain optically active compounds (illustratively, such compounds include optically active biphenyls) and/or dichroic coloring substances (e.g., azo, azoxy and anthraquinone coloring substances). The amount of such compounds in the mixtures is determined by the desired pitch, color, extinction, solubility and the like.

The inventive mixtures containing, inter alia, Compound I and other liquid crystalline and/or non-liquid crystalline compounds can be manufactured by conventional procedures. Illustratively, a mixture of the desired components can be heated to a temperature barely above the clearing point and subsequently cooled down.

In another aspect of the invention, Compound I (which is miscible with all known liquid crystals) can be used in all customary electro-optical devices. The choice of the components of the mixture generally depends on the purpose.

An electro-optical device containing one or more compounds of the formula I can be manufactured in a known manner. Illustratively, the device can be produced by evacuating a suitable cell and introducing the inventive compound or mixture into the evacuated cell.

The invention is also concerned with all novel compounds mixtures, processes, uses and devices as herein described.

The following non-limiting Examples illustrate the invention. In particular, Examples 18–29 describe preferred nematic mixtures. Unless otherwise stated, percentages and ratios of solvent mixtures are given in volume and the temperatures are expressed in degrees Centigrade. Room temperature is 23° C. The ether is diethyl ether and the alcohol is ethanol. One bar pressure is 0.987 atmospheres. The compounds of formula I named in the Examples as well as the corresponding starting materials are racemates unless expressly indicated otherwise. For simplification, however, only the name of one of the optical antipodes usually is specified.

EXAMPLE 1

A mixture of 568 mg of (4a$\alpha$H,8a$\beta$H)-decahydro-6$\beta$-pentyl-2$\alpha$-phenylnaphthalene (purity 97.5%) and 0.30 ml of n-valeryl chloride in 10 ml of methylene chloride was placed while gassing with argon in a 50 ml flask fitted with a reflux condenser and treated portionwise at room temperature with 333 mg of aluminum chloride. After completion of the addition (about 10 minutes), the mixture was stirred at room temperature for a further 45 minutes and under reflux for 30 minutes. Subsequently, the flask content was poured into 15 ml of ice-cold 2 N hydrochloric acid and extracted three times with 20 ml of methylene chloride each time. The organic phases were washed twice with 15 ml of 3 N sodium hydroxide each time, three times with 20 ml of water each time and once with 20 ml of saturated sodium bicarbonate solution, dried over magnesium sulphate and concentrated. The residual, crystallizing oil (736 mg, 100%) contained 93.3% of 4'-[(4a$\alpha$H,8a$\beta$H)-decahydro-6$\beta$-pentyl-2$\alpha$-naphthyl]valerophenone as well as 4.1% of the corresponding ortho isomer in accordance with gas chromatographical analysis. Repeated crystallization from methanol gave analytically pure materials; m.p. 63.4° C., cl.p. 104.0° C.; Rf value 0.34 (3% ethyl acetate/97% petroleum ether).

The (4a$\alpha$H,8a$\beta$H)-decahydro-6$\beta$-pentyl-2$\alpha$-phenylnaphthalene used as the starting material was prepared as follows:

(a) A mixture of 174 g of 4-phenylcyclohexanone and 149 ml of pyrrolidine, freshly distilled over potassium hydroxide, in 700 ml of benzene was heated to reflux for 17 hours while gassing with argon in a 1.5 l sulphonation flask fitted with a water separator, thermometer and reflux condenser and 18 ml of water was separated. Subsequently, benzene as well as excess pyrrolidine was distilled off firstly at normal pressure and then at 12 mmHg and 0.1 mmHg and the residual, crystalline enamine was dissolved in 700 ml of benzene. The resulting homogeneous solution was now treated dropwise while cooling with ice during 70 minutes with 86.6 ml of freshly distilled methyl vinyl ketone so that the internal temperature did not exceed 25° C. After completion of the addition, the mixture was heated to reflux for a further 18 hours, subsequently treated with a buffer solution (pH 5) of 68 g of sodium acetate trihydrate in 83 ml of acetic acid and 83 ml of water and again heated to reflux for 4 hours. After cooling, the mixture was extracted twice with 300 ml of ether each time and the extract was washed twice with 300 ml of 2 N hydrochloric acid each time, once with 400 ml of saturated sodium bicarbonate solution and once with 300 ml of saturated sodium chloride solution, dried over magnesium sulphate and concentrated. The resulting brown oil (225 g) contained 11.4% of 4-phenylcyclohexanone, 17.8% of 1,2,3,4,5,6,7,8-octahydro-2-oxo-6-phenylnaphthalene, 61.3% of 2,3,4,4a$\beta$,5,6,7,8-octahydro-2-oxo-6$\alpha$-phenylnaphthalene as well as further high molecular weight compounds in accordance with gas chromatographical analysis. Fractional distillation and crystallization from hexane gave 99.1 g of colorless crystals containing 91.6% of 2,3,4,4a$\beta$,5,6,7,8-octahydro-2-oxo-6$\alpha$-phenylnaphthalene (repeated crystallization gave a purity of about 97%). The mother liquor was concentrated and the residual crystalline mass was dissolved in a mixture of 300 ml of tetrahydrofuran and 200 ml of 2 N hydrochloric acid and heated to reflux for 6 hours. Subsequently, the mixture was extracted twice with 200 ml of ether each time and the extract was washed with 200 ml of saturated sodium bicarbonate solution and 200 ml of sodium chloride solution, dried over magnesium sulphate and concentrated. Fractional crystallization from hexane gave a further 33.6 g of colorless crystals of 2,3,4,4a$\beta$,5,6,7,8-octahydro-2-oxo-6$\alpha$-phenylnaphthalene. Total yield 54.2%. M.p. 78°–79° C.

(b) 280 ml of ammonia were condensed at −78° C. while gassing with argon in a 750 ml sulphonation flask fitted with a dry-ice condenser, dropping funnel and stirrer (of glass) and treated with 1.6 g of lithium wire cut into small pieces. The deep blue solution was stirred for a further 15 minutes and subsequently treated at −33° C. with a solution of 15.0 g of 2,3,4,4a$\beta$,5,6,7,8-octahydro-2-oxo-6$\alpha$-phenylnaphthalene (purity 92.5%) in 5.5 ml of t-butanol and 50 ml of ether. Subsequently, the mixture was stirred for a further 2 minutes, then solid ammonium chloride was added cautiously in order to destroy excess lithium, and the ammonia was evaporated. The residual, semi-crystalline mass was distributed in 300 ml of water and 300 ml of ether, the aqueous phase was separated and extracted a further twice with 300 ml of ether each time. The organic phases were washed twice with 200 ml of water each time and once with 300 ml of saturated sodium chloride solution, dried over magnesium sulphate and concentrated. The crude product obtained (14.0 g), which besides the main product (4aβH,8aαH)-decahydro-2-oxo-6α-phenylnaphthalene still contained the corresponding diastereomeric alcohol, was dissolved in 120 ml of acetone and treated at 0° C. with an excess of 8 N chromic acid $H_2CrO_4$ [Org. Synth. 42, 79 (1962)]. Subsequently, the mixture was stirred for a further 15 minutes, excess oxidizing agent was destroyed with isopropanol, the mixture was filtered and back-washed with acetone. The filtrate was concentrated, the residue was distributed in 300 ml of water and 300 ml of ether, the aqueous phase was separated and extracted a further twice with 200 ml of ether each time. The organic phases were washed twice with 200 ml of water each time and once with 300 ml of saturated sodium chloride solution, dried over magnesium sulphate and concentrated. Fractional distillation of the yellow oil obtained (13.0 g) gave in the main run (0.04 mmHg/130°-139° C.) 11.5 g of (4aβH,8aαH)-decahydro-2-oxo-6α-phenylnaphthalene as a crystallizing, colorless oil with a purity of 94.4%. By recrystallization from hexane there was obtained pure ketone; m.p. 55.2° C.; Rf value 0.43 [toluene/ethyl acetate (9:1)]. Yield 76.3%.

(c) 6.33 g of (4aβH,8aαH)-decahydro-2-oxo-6α-phenylnaphthalene (purity 92%) and 5.47 g of toluene-4-sulphonylmethyl isocyanide in 100 ml of dimethoxyethane were placed while gassing with argon at about −5° C. in a 350 ml sulphonation flask fitted with a thermometer and dropping funnel and treated with a warm suspension of 5.66 g of potassium t-butylate in 20 ml of t-butanol so that the internal temperature did not exceed 0° C. After completion of the addition, the dropping funnel was rinsed with 2 ml of t-butanol. The mixture was warmed to 25° C. (a voluminous precipitate beginning to separate out) and stirred at this temperature for 75 minutes. Subsequently, the majority of the solvent was removed on a rotary evaporator and the residue was poured into 100 ml of water and extracted three times with 100 ml of petroleum ether each time. The organic phases were washed with 100 ml of water and with 100 ml of saturated sodium chloride solution, dried over magnesium sulphate and concentrated. The residual, yellowish oil (6.15 g) which contained 46% of (4aβH,8aαH)-decahydro-6α-phenylnaphthalene-2β-carbonitrile and 50.8% of -2α-carbonitrile in accordance with gas chromatographical analysis was used in the following step without further purification.

(d) 1.36 g of magnesium shavings were covered with 10 ml of dry ether while gassing with argon in a dry 200 ml sulphonation flask fitted with a thermometer, reflux condenser and dropping funnel and, after the addition of an iodine crystal, treated dropwise with a solution of 6.03 ml of n-butyl bromide in 40 ml of dry ether so that a slight reflux was maintained. After completion of the addition, the mixture was stirred for a further 30 minutes and then a solution of 6.15 g of the nitrile mixture described in paragraph (c) in 40 ml of dry ether was added dropwise within 5 minutes. The resulting mixture was now heated to reflux for 18 hours, subsequently treated carefully with 50 ml of 2 N hydrochloric acid and again heated to reflux for 1 hour. The aqueous phase was separated and extracted a further twice with 200 ml of ether each time. The organic phases were washed with 200 ml of saturated sodium bicarbonate solution and with 200 ml of saturated sodium chloride solution, dried over magnesium sulphate and concentrated. The resulting, crystallizing oil (7.54 g) which contained 93.8% of (4aβH,8aαH)-decahydro-6α-phenyl-2β-valerylnaphthalene, 1.3% of the corresponding 2α-valeryl compound as well as 0.9% of (4aβH,8aαH)-decahydro-6α-phenylnaphthalene-2-carbonitrile in accordance with gas chromatographical analysis was used in the following step without further purification. By additional recrystallization from methanol there could be obtained pure (4aβH,8aαH)-decahydro-6α-phenyl-2β-valerylnaphthalene; m.p. 58°-59° C.; Rf value 0.80 (10% ethyl acetate/90% petroleum ether).

(e) A mixture of 7.54 g of the crude (4aβH,8aαH)-decahydro-6α-phenyl-2β-valerylnaphthalene described in paragraph (d), 2.72 ml of hydrazine hydrate, 30 ml of diethyleneglycol and 30 ml of ethanol was heated to reflux for 105 minutes while gassing with argon in a 100 ml round flask fitted with a reflux condenser. Then, after adding 3.37 g of solid potassium hydroxide, the mixture was heated successively to 225° C. (with distillation of the ethanol) and held at this temperature for 2.5 hours. The cooled mixture was taken up in 200 ml of water and extracted three times with 200 ml of petroleum ether each time. The organic phases were washed twice with 200 ml of water each time, dried over magnesium sulphate and concentrated. Chromatography of the resulting crystallizing oil (6.64 g) with hexane on a short column of silica gel gave 5.65 g of (4aαH,8aβH)-decahydro-6β-pentyl-2α-phenylnaphthalene (purity 97.5%) as colorless crystals; m.p. 54°-55° C. Rf values (hexane): educt 0.05, product 0.44. Total yield based on (4aβH,8aαH)-decahydro-2-oxo-6α-phenylnaphthalene 78.5%.

The starting material of formula IVa in which $R^6$ signifies methyl (for the preparation of the 6β-methyl compounds) can not be prepared according to the foregoing process. This compound was prepared as follows:

A suspension of 95 mg of lithium aluminium hydride in 10 ml of absolute tetrahydrofuran was placed under an argon atmosphere in a 100 ml round flask fitted with a reflux condenser and dropping funnel, treated with a solution of 1.00 g of (4aβH,8aαH)-decahydro-6α-phenyl-2β-(tosyloxymethyl)naphthalene (prepared according to Example 15) in 10 ml of absolute tetrahydrofuran and subsequently heated to reflux for 18 hours. Then, 10 ml of 2 N hydrochloric acid were added cautiously and the separated aqueous phase was extracted a further twice with 30 ml of ether each time. The organic phases were washed twice with 30 ml of water each time, dried over magnesium sulphate and concentrated. Chromatography of the resulting crude product (560 mg) with hexane on a short column of silica gel gave 528 mg (92%) of (4aαH,8aβH)-decahydro-6β-methyl-2α-phenylnaphthalene as a crystallizing oil (purity 99.9%); m.p. 43.7° C. Rf value (hexane): 0.74.

The following compounds can be prepared in analogous manner:

4'-[(4aαH,8aβH)-Decahydro-6β-methyl-2α-naphthyl propiophenone; m.p. 83.8° C., cl.p. 79.0° C. (monotropic).

4'-[(4aαH,8aβH)-Decahydro-6β-methyl-2α-naphthyl]valerophenone; m.p. 58.8° C., cl.p. 62.0° C.

4'-[(4aαH,8aβH)-Decahydro-6β-ethyl-2α-naphthyl]-valerophenone; three modifications with m.p. 44.8° C., 49.2° C. and 61.6° C., cl.p. 76° C.

4'-[(4aαH,8aβH)-Decahydro-6β-propyl-2α-naphthyl]-acetophenone; m.p. 70.5° C., cl.p. 92.5° C.

4'-[(4aαH,8aβH)-Decahydro-6β-propyl-2α-naphthyl]-propiophenone; m.p. 69.7° C., cl.p. 122.5° C.

4'-[(4aαH,8aβH)-Decahydro-6β-propyl-2α-naphthyl]-valerophenone; m.p. 52.8° C., cl.p. 96.8° C.

4'-[(4aαH,8aβH)-Decahydro-6β-propyl-2α-naphthyl]-heptanophenone; m.p. 62.4° C., cl.p. 99.2° C.

4'-[(4aαH,8aβH)-Decahydro-6β-butyl-2α-naphthyl]-valerophenone; m.p. 70.2° C., cl.p. 97.5° C.

4'-[(4aαH,8aβH)-Decahydro-6β-pentyl-2α-naphthyl]-acetophenone; m.p. 68.3° C., cl.p. 97.1° C.

4'-[(4aαH,8aβH)-Decahydro-6β-pentyl-2α-naphthyl]-propiophenone; m.p. 75.2° C., cl.p. 125.7° C.

4'-[(4aαH,8aβH)-Decahydro-6β-pentyl-2α-naphthyl]-butyrophenone; m.p. 59.8° C., cl.p. 95.7° C.

4'-[(4aαH,8aβH)-Decahydro-6β-heptyl-2α-naphthyl]-propiophenone; m.p. 60.1° C., cl.p. 122.0° C.

(4aαH,8aβH)-Decahydro-6β-ethyl-2α-phenylnaphthalene; m.p. 29.9° C.

(4aαH,8aβH)-Decahydro-6β-propyl-2α-phenylnaphthalene; m.p. 64° C.

(4aαH,8aβH)-Decahydro-6β-butyl-2α-phenylnaphthalene; m.p. 43.5°–45.2° C.

(4aαH,8aβH)-Decahydro-6β-heptyl-2α-phenylnaphthalene.

(4aβH,8aαH)-Decahydro-6α-phenyl-2β-propionylnaphthalene; m.p. 52°–54° C.

(4aβH,8aαH)-Decahydro-6α-phenyl-2β-butyrylnaphthalene; m.p. 52.2°–54.6° C.

EXAMPLE 2

A mixture of 354 mg of crude product containing 68% of (4aαH,8aβH)-decahydro-6β-pentyl-2α-(p-bromophenyl)-naphthalene, 107.5 mg of copper (I) cyanide and one drop of pyridine in 4 ml of dry dimethylformamide was heated to reflux under an argon atmosphere for 24 hours in a 25 ml round flask fitted with a reflux condenser. The cooled mixture was subsequently poured into 10 ml of 30% sodium cyanide solution and extracted three times with 30 ml of ether each time. The organic phases were washed three times with 20 ml of water each time, dried over potassium carbonate and concentrated. Low pressure chromatography (0.5 bar) of the residual oil (281 mg) on 20 g of silica gel using hexane/toluene (2:1) as the eluant gave, in the order of elution, 29 mg of o-[(4aαH,8aβH)-decahydro-6β-pentyl-2α-naphthyl]benzonitrile, 29 mg of a mixture of the o- and the p-substituted benzonitriles and 140 mg of the desired p-[(4aαH,8aβH)-decahydro-6β-pentyl-2α-naphthyl]benzonitrile which formed colorless crystals of melting point 71.7° C. and clearing point 124.5° C. after evaporation of the solvent. Rf values [hexane/toluene (2:1)]: o-[(4aαH,8aβH)-decahydro-6β-pentyl-2α-naphthyl]benzonitrile 0.27, p-[(4aαH,8aβH)-decahydro-6β-pentyl-2α-naphthyl]benzonitrile 0.19.

The crude product containing (4aαH,8aβH)-decahydro-6β-pentyl-2α-(p-bromophenyl)naphthalene used as the starting material was prepared as follows:

A mixture of 284 mg of (4aαH,8aβH)-decahydro-6β-pentyl-2α-phenylnaphthalene (prepared according to Example 1) and 60 mg of iron powder in 5 ml of carbon tetrachloride was placed under an argon atmosphere in a 25 ml flask fitted with a reflux condenser and dropping funnel and treated dropwise under reflux within 15 minutes with 1.15 ml of a 1 N solution of bromine in carbon tetrachloride. After completion of the addition, the mixture was heated to reflux for a further 80 minutes and subsequently poured into 10 ml of 10% sodium thiosulphate solution and extracted twice with 20 ml of chloroform each time. The organic phases were washed with 20 ml of 1 N sodium hydroxide and with 20 ml of saturated sodium chloride solution, dried over potassium carbonate and concentrated. The residual, crystallizing oil (354 mg) which contained 12% of (4aαH,8aβH)-decahydro-6β-pentyl-2α-phenylnaphthalene, 68% of (4aαH,8aβH)-decahydro-6β-pentyl-2α-(p-bromophenyl)-naphthalene and 15.4% of the corresponding ortho isomer in accordance with gas chromatographical analysis could be used in the process described in the first paragraph of this Example without further purification. Rf values (hexane): educt 0.44, products 0.51 and 0.38.

The following compounds can be prepared in an analogous manner:

p-[(4aαH,8aβH)-Decahydro-6β-methyl-2α-naphthyl]benzonitrile; m.p. 88.5° C., cl.p. 73.9° C. (monotropic).

p-[(4aαH,8aβH)-Decahydro-6β-ethyl-2α-naphthyl]-benzonitrile; m.p. 74.5° C., cl.p. 95.5° C.

p-[(4aαH,8aβH)-Decahydro-6β-propyl-2α-naphthyl]benzonitrile; m.p. 77.3° C., cl.p. 126.5° C.

p-[(4aαH,8aβH)-Decahydro-6β-butyl-2α-naphthyl]-benzonitrile; m.p. 61.3° C., cl.p. 116° C.

p-[(4aαH,8aβH)-Decahydro-6β-heptyl-2α-naphthyl]benzonitrile; m.p. 78.6° C., cl.p. 117.5° C.

EXAMPLE 3

2.70 g of 4'-[(4aαH,8aβH)-decahydro-6β-pentyl-2α-naphthyl]acetophenone (prepared analogously to Example 1) in 33 ml of dioxan were placed at room temperature under an argon atmosphere in a 100 ml sulphonation flask fitted with a stirrer, thermometer, reflux condenser and dropping funnel and treated with 23.1 ml of a cold (0°–5° C.) hypobromite solution (separately prepared from 2.1 ml of bromine and 21 ml of 6 N sodium hydroxide). After a few minutes there separated a voluminous precipitate which still increased substantially upon subsequent warming to 50° C. After stirring for a total of 60 minutes (testing for hypobromite negative), the mixture was adjusted to pH 1–2 with about 40 ml of 4 N hydrochloric acid and extracted three times with 100 ml of methylene chloride each time. The organic phases were washed a further twice with 100 ml of water each time and once with 100 ml of saturated sodium chloride solution, dried over magnesium sulphate and concentrated. Crystallization of the solid crude product (3.1 g) from chloroform gave 1.88 g (65%) of p-[(4aαH,8aβH)-decahydro-6β-pentyl-2α-naphthyl]benzoic acid as colorless platelets; m.p. 137.6° C., cl.p. 302.5° C.; Rf value [chloroform/ethyl acetate (1:1)]: 0.23–0.38 (longish spot).

The following compound can be prepared in an analogous manner:

p-[(4aαH,8aβH)-Decahydro-6β-propyl-2α-naphthyl]benzoic acid; m.p. 143.7° C., cl.p. 312.5° C.

EXAMPLE 4

1.05 g of p-[(4aαH,8aβH)-decahydro-6β-pentyl-2α-naphthyl]benzamide were suspended under an argon atmosphere in 9.2 ml of pyridine in a 50 ml round flask fitted with a magnetic stirrer and treated at room temperature with 1.3 ml of benzenesulphonyl chloride. The mixture was stirred at room temperature overnight, subsequently poured into a mixture of 30 g of ice and 30 g of 2 N hydrochloric acid and extracted three times with 100 ml of ether each time. The organic phases were washed once with 50 ml of 2 N hydrochloric acid and twice with 100 ml of water each time, dried over magnesium sulphate and concentrated. Low pressure chromatography (0.5 bar) of the crude product (968 mg) on silica gel using 3% ethyl acetate/97% petroleum ether as the eluant gave 931 mg (94%) of p-[(4aαH,-8aβH)-decahydro-6β-pentyl-2α-naphthyl]benzonitrile as a colorless, crystallizing oil (purity 96%). Recrystallization from methanol yielded analytically pure material; m.p. 71.7° C., cl.p. 124.5° C.; Rf value (3% ethyl acetate/97% petroleum ether): 0.33.

The p-[(4aαH,8aβH)-decahydro-6β-pentyl-2α-naphthyl]benzamide used as the starting material was prepared as follows:

A mixture of 1.88 g of p-[(4aαH,8aβH)-decahydro-6β-pentyl-2α-naphthyl]benzoic acid prepared according to Example 3) and 1.03 ml of triethylamine in 27 ml of chloroform was treated at 0° C. with 0.75 ml of ethyl chloroformate under an argon atmosphere in a 100 ml sulphonation flask fitted with a stirrer, thermometer, reflux condenser and gas inlet. Subsequently, the homogeneous solution was stirred at 0° C. for a further 15 minutes and then a strong stream of ammonia was conducted in for 10 minutes. Thereby, a voluminous precipitate immediately resulted. The mixture was stirred for a further 1 hour, thereafter rinsed with chloroform into a 250 ml round flask and concentrated to dryness in vacuo. The residual, solid residue was suspended in 25 ml of water, filtered, washed with water and dried overnight at 50° C./12 mmHg over potassium hydroxide. There were obtained 1.08 g (58%) of crude p-[(4aαH,-8aβH)-decahydro-6β-pentyl-2α-naphthyl]benzamide as a colorless powder which formed colorless crystals of melting point 232°–235° C. after a single crystallization from chloroform. Rf values [chloroform/ethyl acetate (1:1)]: educt 0.23–0.38 (longish spot), product 0.28.

All benzonitriles described in Example 2 can be prepared in an analogous manner.

EXAMPLE 5

A mixture of 0.32 ml of absolute methanol and 7.5 ml of absolute pyridine was placed at 3° C. while gassing with argon in a 100 ml sulphonation flask fitted with a dropping funnel and thermometer and treated dropwise with a solution of p-[(4aαH,4aβH)-decahydro-6β-pentyl-2α-naphthyl]benzoic acid chloride [obtained by boiling 2.46 g of p-[(4aαH,8aβH)-decahydro-6β-pentyl-2α-naphthyl]benzoic acid, prepared in accordance with Example 3, in 15 ml of thionyl chloride for 2 hours and subsequently removing the excess thionyl chloride in vacuo] in 10 ml of absolute benzene. After completion of the addition, the mixture was left to stand at room temperature overnight, subsequently poured into a mixture of 15 g of ice and 15 ml of concentrated hydrochloric acid and extracted three times with 50 ml of ether each time. The organic phases were washed once with 12 ml of ice-cold 1 N sodium hydroxide and twice with 50 ml of water each time, dried over magnesium sulphate and concentrated. Crystallization of the residual, crystalline mass from methanol gave p-[(4aαH,8aβH)-decahydro-6β-pentyl-2αnaphthyl]benzoic acid methyl ester as colorless crystals; m.p. 60.4° C., cl.p. 111.5° C.; Rf value (toluene): 0.43.

Methyl esters can also be prepared according to the following procedure:

51 mg of p-[(4aαH,8aβH)-decahydro-6β-pentyl-2α-naphthyl]benzoic acid (prepared in accordance with Example 3) were dissolved in 10 ml of ether in an unground 25 ml flask and treated at room temperature with a solution of diazomethane in ether until the yellow color of the diazomethane remained. Subsequently, the solvent and excess diazomethane were distilled off and the crystalline residue were recrystallised from methanol. There were obtained 46.0 mg (87%) of p-[(4aαH,8aβH)-decahydro-6β-pentyl-2α-naphthyl]benzoic acid methyl ester as colorless crystals; m.p. 60.4° C., cl.p. 111.5° C.; Rf value (toluene): 0.43.

The following compound can be prepared in an analogous manner:

p-[(4aαH,8aβH)-Decahydro-6β-pentyl-2α-naphthyl]benzoic acid propyl ester; m.p. 52.0° C., cl.p. 73.9° C.

EXAMPLE 6

A mixture of 327 mg of 4'-[(4aαH,8aβH)-decahydro-6β-pentyl-2α-naphthyl]acetophenone (prepared analogously to Example 1) and 383 mg of 3-chloroperbenzoic acid (about 90%) in 10 ml of methylene chloride was stirred in the dark at room temperature for 46 hours under argon atmosphere in a 25 ml round flask. Subsequently, the flask content was poured into 10 ml of 10% sodium thiosulphate solution and the aqueous phase was extracted a further twice with 20 ml of methylene chloride each time. The organic phases were washed twice with 20 ml of saturated sodium bicarbonate solution each time, dried over potassium carbonate and concentrated. Low pressure chromatography (0.4 bar) of the crude product (337 mg) on silica gel using a mixture of 3% ethyl acetate/97% petroleum ether as the eluant gave 252 mg (74%) of p-[4aαH,8aβH)-decahydro-6β-pentyl-2α-naphthyl]phenylacetate as a colorless crystallizing oil. A single crystallization from methanol yielded analytically pure material; m.p. 56.1° C., cl.p. 102.1° C. Rf values (toluene): educt 0.29, product 0.45.

The following compound can be prepared in an analogous manner:

p-[(4aαH,8aβH)-Decahydro-6β-pentyl-2α-naphthyl]phenylpropionate; m.p. 57.7° C., cl.p. 110.0° C.

EXAMPLE 7

160 mg of p-[(4aαH,8aβH)-decahydro-6β-pentyl-2α-naphthyl]phenol, 0.277 ml of n-butyl iodide, 276 mg of finely ground potassium carbonate and 6 ml of acetone were boiled for 70 hours while stirring under an argon atmosphere in a 25 ml round flask fitted with a reflux condenser. The cooled mixture was subsequently poured into 50 ml of water and extracted three times with 50 ml of ether each time. The organic phases were washed once with 20 ml of 2 N sodium hydroxide, dried over potassium carbonate and concentrated. A single crystallization of the product obtained from methanol gave 135 mg (71%) of (4aαH,8aβH)-decahydro-2α-(p-butyloxyphenyl-6β-pentylnaphthalene as colorless needles; m.p. 70.2° C., cl.p. 96.0° C.; Rf value (hexane): 0.16.

The p-[(4aαH,8aβH)-decahydro-6β-pentyl-2αnaphthyl]phenol used as the starting material was prepared as follows:

50 mg of lithium aluminium hydride in 2 ml of dry ether were placed under an argon atmosphere in a 25 ml flask fitted with a reflux condenser and treated dropwise with a solution of 197 mg of p-[(4aαH,8aβH)-decahydro-6β-pentyl-2α-naphthyl]phenylacetate (prepared according to Example 6) in 6 ml of dry ether. Subsequently, the mixture was stirred at room temperature for a further 2 hours, then the flask content was poured into 10 ml of 1 N sulphuric acid, the aqueous phase was separated and extracted twice with 20 ml of ether each time. The organic phases were washed with 20 ml of saturated sodium chloride solution, dried over magnesium sulphate and concentrated. There were obtained 165 mg (95%) of p-[(4aαH,8aβH)-decahydro-6β-pentyl-2α-naphthyl]phenol as colorless crystals; m.p. 148°–149° C. Rf values (10% ethyl acetate/90% petroleum ether): educt 0.46, product 0.19.

The following compound can be prepared in an analogous manner:

(4aαH,8aβH)-Decahydro-2α-(p-propyloxyphenyl)-6β-pentylnaphthalene; m.p. 62.9° C., cl.p. 89.9° C.

EXAMPLE 8

A mixture of 258 mg of 4'-[(4aαH,8aβH)-decahydro-6β-pentyl-2α-naphthyl]valerophenone (prepared according to Example 1), 0.070 ml of hydrazine hydrate, 1 ml of diethyleneglycol and 1 ml of ethanol was heated to reflux for 90 minutes while gassing with argon in a 10 ml round flask fitted with a reflux condenser. Then, 84 mg of solid potassium hydroxide were added, the mixture was heated to 220° C. within about 15 minutes with distillation of the ethanol and held at this temperature for 2 hours. The cooled mixture was taken up in 20 ml of water and extracted three times with 20 ml of petroleum ether each time. The organic phases were washed twice with 20 ml of water each time, dried over magnesium sulphate and concentrated. Chromatography of the yellow oil obtained (237 mg) with hexane on a short column of silica gel gave 205 mg (83%) of (4aαH,8aβH)-decahydro-2α-(p-pentylphenyl)-6β-pentylnaphthalene as a colorless crystallizing oil. By a single crystallization from methanol there was obtained analytically pure material; m.p. 39.9° C., cl.p. 59.7° C.; Rf value (hexane): 0.52.

The reduction of the carbonyl group can also be carried out by catalytic hydrogenation when ring A in the compound of formula Ia or Ib is aromatic:

50 mg of 10% palladium/carbon in 10 ml of absolute ethanol were pre-hydrogenated at normal pressure and room temperature for 10 minutes in a 50 ml sulphonation flask. Then, a solution of 350 mg of 4'-[(4aαH,8aβH)-decahydro-6β-propyl-2α-naphthyl]heptanophenone (prepared according to Example 1) in 10 ml of absolute ethanol was added and the mixture was hydrogenated at normal pressure and room temperature for 3 hours. After filtering the mixture, removing the solvent on a rotary evaporator, taking up the residual crude product in 50 ml of ether, again filtering and concentrating, there were obtained 316 mg (94%) of (4aαH,8aβH)-decahydro-2α-(p-heptylphenyl)-6β-propylnaphthalene as a crystallizing oil (purity 96.3%). Additional crystallization from methanol gave analytically pure material; m.p. 49.1° C., cl.p. 47.4° C. (monotropic); Rf value (hexane): 0.51.

The aldehydes required as the starting materials for the preparation of the 2α-(p-methylphenyl) compounds can be obtained as follows:

A solution of 518 mg of p-[(4aαH,8aβH)-decahydro-6β-pentyl-2α-naphthyl]benzonitrile (prepared according to Example 2 or Example 4) in 20 ml of toluene was placed at 0° C. under an argon atmosphere in a 100 ml sulphonation flask fitted with a thermometer and magnetic stirrer and treated with 1.6 ml of a 20% solution of diisobutylaluminium hydride in toluene so that the internal temperature did not exceed 5° C. After completion of the addition, the mixture was stirred at 0° C. for a further 30 minutes and at room temperature for 100 minutes, subsequently treated cautiously with 25 ml of 2 N sulphuric acid and extracted three times with 100 ml of chloroform each time. The organic phases were washed twice with 50 ml of water each time and once with 50 ml of saturated sodium chloride solution, dried over magnesium sulphate and concentrated. Repeated crystallization of the quantitatively obtained crude product (purity 95%) from hexane gave p-[(4aαH,8aβH)-decahydro-6β-pentyl-2-α-naphthyl]benzaldehyde as colorless crystals; m.p. 55° C., cl.p. 98.8° C.; Rf values [petroleum ether/ethyl acetate (97:3)]: educt 0.26. product 0.18.

The following compounds can be prepared in an analogous manner:

(4aαH,8aβH)-Decahydro-2α-(p-ethylphenyl)-6β-propylnaphthalene; m.p. 37.2° C.

(4aαH,8aβH)-Decahydro-2α-(p-propylphenyl)-6β-propylnaphthalene; m.p. 31.8° C., cl.p. 44.0° C.

(4aαH,8aβH)-Decahydro-2α-(p-pentylphenyl)-6β-propylnaphthalene; m.p. 33.2° C. or 35.0° C. (two modifications), cl.p. 45.2° C.

(4aαH,8aβH)-Decahydro-2α-(p-heptylphenyl)-6β-propylnaphthalene; m.p. 49.1° C., cl.p. 47.4° C. (monotropic).

(4aαH,8aβH)-Decahydro-2α-(p-methylphenyl)-6β-pentylnaphthalene; m.p. 49.5° C., cl.p. 61.0° C.

(4aαH,8aβH)-Decahydro-2α-(p-ethylphenyl)-6β-pentylnaphthalene; m.p. 27.9° C., cl.p. 46.0° C.

(4aαH,8aβH)-Decahydro-2α-(p-propylphenyl)-6β-pentylnaphthalene; m.p. 39.6° C., cl.p. 56.9° C.

(4aαH,8aβH)-Decahydro-2α-(p-butylphenyl)-6β-pentylnaphthalene; m.p. 34.4° C., cl.p. 48.4° C.

(4aαH,8aβH)-Decahydro-2α-(propylphenyl)-6β-heptylnaphthalene; m.p. 44.6° C., cl.p. 65.3° C.

EXAMPLE 9

272 mg of crude product containing (4aαH,8aβH)-decahydro-6β-pentyl-2α-[4-(1-hydroxypropyl)cyclohexyl]naphthalene were dissolved in 10 ml of acetone and treated at 25° C. with an excess of 8 N chromic acid $H_2CrO_4$ (until the orange-yellow color remained). Subsequently, the mixture was stirred for a further 30 minutes, excess oxidizing agent was destroyed with isopropanol and the green mixture and distributed in 50 ml of water and 50 ml of ether. The aqueous phase was separated and extracted twice with 50 ml of ether each time. The organic phases were washed twice with 50 ml of water each time, dried over magnesium sulphate and concentrated. The resulting, crystalline crude product (263 mg) which contained 23.6% of (4aαH,8aβH)-decahydro-2α-(trans-4-propionylcyclohexyl)-6β-pentylnaphthalene, 67.9% of cis isomer and 7.4% of (4aαH,8aβH)-decahydro-2α-(trans-4-propylcyclohexyl)-6β-pentylnaphthalene in accordance with gas chromatographical analysis was suspended in 10 ml of 1 N methanol potassium hydroxide solution in a 25 ml round flask fitted with a reflux condenser and heated to reflux overnight. Subsequently, the mixture was concentrated to dryness and the residue was taken up in 30 ml of 1 N hydrochloric acid and 50 ml of ether. The aqueous phase was separated and extracted a further twice with 50 ml of ether each time. The organic phases were washed twice with 30 ml of water each time, dried over magnesium sulphate and concentrated. The crude product obtained (245 mg) contained 86% of (4aαH,8aβH)-decahydro-2α-(trans-4-propionylcyclohexyl)-6β-pentylnaphthalene, 5.4% of the cis isomer and 7.5% of (4aαH,8aβH)-decahydro-2α-(trans-4-propylcyclohexyl)-6β-pentylnaphthalene. Separation of this crude product by low pressure chromatography (0.4 bar) on silica gel using 3% ethyl acetate/97% petroleum ether as the eluant gave 207 mg (60%) of (4aαH,-

8aβH)-decahydro-2α-(trans-4-propionylcyclohexyl)-6β-pentylnaphthalene as colorless crystals (purity 95%). Additional crystallization from ethyl acetate yielded analytically pure material; m.p. 98.3° C., cl.p. 147° C. Rf values (3% ethyl acetate/97% petroleum ether): 4'-[(4aαH,8aβH)-decahydro-6β-pentyl-2α-naphthyl]propiophenone 0.28, (4a αH,8aβH)-decahydro-6β-pentyl-2α-[4-(1-hydroxypropyl)cyclohexyl]naphthalene 0.11, (4aαH,8aβH)-decahydro-2α-(cis-4-propionylcyclohexyl)-6β-pentylnaphthalene 0.33, (4aαH,8aβH)-decahydro-2α-(trans-4-propionylcyclohexyl)-6β-pentylnaphthalene 0.27.

The crude product containing (4aαH,8aβH)-decahydro-6β-pentyl-2α-[4-(1-hydroxypropyl)cyclohexyl]naphthalene used as the starting material was prepared as follows:

340 mg of 4'-[(4aαH,8aβH)-decahydro-6β-pentyl-2α-naphthyl]propiophenone (prepared analogously to Example 1) dissolved in 120 ml of ethanol were hydrogenated in the presence of 1.5 g of 5% rhodium-/aluminium oxide at 25° C. and 50 bar for 22 hours. After filtering off the catalyst and concentrating the filtrate on a rotary evaporator, there were obtained 272 mg of crystalline crude product which in accordance with thin-layer and gas chromatography contained no starting material, but instead mainly the diastereomeric alcohols of (4aαH,8aβH)-decahydro-6β-pentyl-2α-[4-(1-hydroxypropyl)cyclohexyl]naphthalene. This crude product was used in the subsequent oxidation without further purification.

The following compounds can be prepared in an analogous manner:

(4aαH,8aβH)-Decahydro-2α-(trans-4-propionylcyclohexyl)-6β-heptylnaphthalene; m.p. 107.5° C., cl.p. 141.2° C.

(4aαH,8aβH)-Decahydro-2α-(trans-4-butyrylcyclohexyl)-6β-pentylnaphthalene; m.p. 92.5° C., cl.p. 138.2° C.

(4aαH,8aβH)-Decahydro-2α-(trans-4-valerylcyclohexyl)6β-propylnaphthalene; m.p. 100.4° C., cl.p. 136.2° C.

(4aαH,8aβH)-Decahydro-2α-(trans-4-valerycyclohexyl)-6β-pentylnaphthalene; m.p. 89.3° C., cl.p. 138.6° C.

(4aαH,8aβH)-Decahydro-2α-(trans-4-heptanoylcyclohexyl)-6β-propylnaphthalene; m.p. 94.3° C., cl.p. 128.5° C.

EXAMPLE 10

A mixture of 139 mg of (4aαH,8aβH)-decahydro-2α-(trans-4-propionylcyclohexyl)-6β-pentylnaphthalene (prepared according to Example 9), 0.46 ml of hydrazine hydrate, 5 ml of diethyleneglycol and 5 ml of ethanol was heated to reflux for 45 minutes under an argon atmosphere in a 25 ml round flask fitted with a reflux condenser. Then, 190 mg of solid potassium hydroxide were added and the mixture was heated to 220° C. within about 15 minutes with distillation of the ethanol and held at this temperature for 3 hours. The cooled mixture was taken up in 100 ml of water and extracted three times with 100 ml of petroleum ether each time. The organic phases were washed twice with 100 ml of water each time, dried over magnesium sulphate and concentrated. Chromatography of the crystalline crude product obtained with hexane on a short column of silica gel gave 126 mg (95%) of (4aαH,8aβH)-decahydro-2α-(trans-4-propylcyclohexyl)-6β-pentylnaphthalene as colorless platelets (purity<99%). Crystallization from acetone yielded analytically pure material; m.p. 76.8° C., cl.p. 136.5° C.; Rf value (hexane): 0.64.

The following compounds can be prepared in an analogous manner:

(4aαH,8aβH)-Decahydro-2α-(trans-4-pentylcyclohexyl)-6β-propylnaphthalene; m.p. 77.8° C., cl.p. 138.0° C.

(4aαH,8aβH)-Decahydro-2α-(trans-4-heptylcyclohexyl)-6β-propylnaphthalene; m.p. 65.4° C., transition smectic A-nematic 79.8° C., cl.p. 131.7° C.

(4aαH,8aβH)-Decahydro-2α-(trans-4-pentylcyclohexyl-6β-pentylnaphthalene; m.p. 70.0° C., transition smectic A-nematic 90.5° C., cl.p. 140.5° C.

(4aαH,8aβH)-Decahydro-2α-(trans-4-propylcyclohexyl)-6β-heptylnaphthalene; m.p. 88.2° C., cl.p. 125.2° C.

EXAMPLE 11

In an analogous manner to Examples 3–7, by converting the alkanoyl group of (4aαH,8aβH)-decahydro-2α-(trans-4-alkanoylcyclohexyl)-6β-alkylnaphthalenes (prepared in accordance with Example 9) into a carboxyl, cyano, alkoxycarbonyl, alkylthiocarbonyl, alkanoyloxy or alkoxy group there can be prepared the corresponding trans-4-[(4aαH,8aβH)-decahydro-6β-alkyl-2α-naphthyl]cyclohexanecarboxylic acids, trans-4-[(4aαH,8aβH)-decahydro-6β-alkyl-2α-naphthyl]cyclohexanecarbonitriles, trans-[(4aαH,8aβH)-decahydro-6β-alkyl-2α-naphthyl]cyclohexanecarboxylic acid alkyl esters, trans-4-[(4aαH,8aβH)-decahydro-6β-alkyl-2α-naphthyl]cyclohexanecarboxylic acid alkylthio esters, trans-4-[(4aαH,8aβH)-decahydro-6β-alkyl-2α-naphthyl]cyclohexylalkanoates or (4aαH,8aβH)-decahydro-2α-(trans-4-alkoxycyclohexyl)-6β-alkylnaphthalenes.

EXAMPLE 12

In an analogous manner to Examples 1–11, starting from (4aαH,8aβH)-decahydro-2α-phenylnaphthalenes there can also be prepared those compounds which have no alkyl group on the decalin structure (i.e. $R^1$=hydrogen in formula I).

The (4aαH,8aβH)-decahydro-2α-phenylnaphthalene starting material can be prepared as follows:

A mixture of 3.5 g of (4aβH,8aαH)-decahydro-2-oxo-6α-phenylnaphthalene (prepared according to Example 1), 1.5 ml of hydrazine hydrate, 15 ml of diethyleneglycol and 15 ml of ethanol was heated to reflux for 2 hours under an argon atmosphere in a 50 ml round flask fitted with a reflux condenser. Then, after adding 1.8 g of solid potassium hydroxide, the mixture was successively heated to 220° C. with distillation of the ethanol and held at this temperature for 2.5 hours. The cooled mixture was taken up in 100 ml of water and extracted three times with 100 ml of petroleum ether each time. The organic phases were washed twice with 100 ml of water each time, dried over magnesium sulphate and concentrated. Chromatography of the liquid crude product obtained with hexane on a short column of silica gel gave 2.70 g (82%) of (4aαH,8aβH)-decahydro-2α-phenylnaphthalene as a colorless oil which began to crystallize upon cooling to 0° C.; m.p. about 16° C.; Rf value (hexane): 0.62.

The following compounds were prepared in this manner:

4'-[(4aαH,8aβH)-Decahydro-2α-naphthyl]-valerophenone; m.p. 42°–43° C.

p-[(4aαH,8aβH)-Decahydro-2α-naphthyl]benzonitrile; m.p. 58.1° C.

(4aαH,8aβH)-Decahydro-2α-(p-pentylphenyl)-naphthalene; m.p. −2° C.

EXAMPLE 13

A mixture of 298.5 mg of (4aβH,8aαH)-decahydro-6α-phenyl-2β-valerylnaphthalene (prepared according to Example 1) and 383 mg of 3-chloroperbenzoic acid (about 90%) in 10 ml of methylene chloride was stirred at room temperature for 5 days under an argon atmosphere and with the exclusion of light in a 25 ml round flask, whereby 3-chlorobenzoic acid began to separate out gradually. Subsequently, the flask content was poured into 10 ml of 10% sodium thiosulphate solution and the aqueous phase was extracted a further twice with 20 ml of methylene chloride each time. The organic phases were washed a further twice with 20 ml of saturated sodium bicarbonate solution each time, dried over potassium carbonate and concentrated. Low pressure chromatography (0.4 bar) of the crude product obtained (303 mg) on silica gel using 3% ethyl acetate/97% petroleum ether as the eluant finally gave 265 mg (84%) of (4aβH,8aαH)-decahydro-6α-phenyl-2β-valeroxy-naphthalene as a colorless oil crystallizing upon cooling. Additional crystallization from methanol yielded analytically pure material; m.p. 33°–34° C. Rf values (toluene): educt 0.41, product 0.47.

EXAMPLE 14

(a) 190 mg of lithium aluminium hydride in 5 ml of ether were placed under an argon atmosphere in a 50 ml flask fitted with a reflux condenser and dropping funnel and treated dropwise with a solution of 500 mg of (4aβH,8aαH)-decahydro-2-oxo-6α-phenylnaphthalene (prepared according to Example 1) in 10 ml of ether. After completion of the addition, the mixture was stirred for a further 30 minutes and then 20 ml of 1 N sulphuric acid were added cautiously. The aqueous phase was separated and extracted a further twice with 50 ml of ether each time. The organic phases were washed twice with 20 ml of water each time, dried over magnesium sulphate and concentrated. There were obtained 495 mg (98%) of colorless crystals consisting of 95% of (4aαH,8aβH)-decahydro-2α-phenyl-6β-hydroxynaphthalene and 5% of -6α-hydroxynaphthalene. Additional crystallization from hexane yielded the 6β-hydroxy compound in 99.8% purity; m.p. 132° C.; Rf value [toluene/ethyl acetate (3:1)]: 0.19.

(b) 72 mg of potassium hydride in 10 ml of absolute dimethoxyethane were placed under an argon atmosphere in a 50 ml flask fitted with a reflux condenser, then treated dropwise with a solution of 66 mg of (4aαH,8aβH)-decahydro-2α-phenyl-6β-hydroxynaphthalene in 5 ml of absolute dimethoxyethane and subsequently stirred at 40° C. for a further 30 minutes. After adding 0.4 ml of butyl iodide, the mixture was heated to reflux for 18 hours. Then, the flask content was poured into 50 ml of water and extracted three times with 50 ml of ether each time. The organic phases were washed with 50 ml of saturated sodium chloride solution, dried over magnesium sulphate and concentrated. Low pressure chromatography (0.4 bar) of the crude product obtained (120 mg) on silica gel using toluene as the eluant gave (4aαH,8aβH)-decahydro-2α-phenyl-6β-butyloxynaphthalene as colorless crystals. Additional crystallization from methanol yielded analytically pure material; m.p. 59.4°–59.6° C.; Rf value (toluene): 0.42.

The (4aαH,8aβH)-decahydro-2α-phenyl-6β-hydroxynaphthalene obtained in paragraph (a) can also be prepared in the following manner:

66 mg of lithium aluminium hydride in 3 ml of dry ether were placed under an argon atmosphere in a 25 ml flask fitted with a reflux condenser and treated dropwise with a solution of 211 mg of (4aβH,8aαH)-decahydro-6α-phenyl-2β-valeroxynaphthalene (prepared according to Example 13) in 10 ml of dry ether. Subsequently, the mixture was stirred at room temperature for a further 2 hours and then the flask content was poured into 20 ml of 2 N sulphuric acid. The aqueous phase was extracted a further twice with 20 ml of ether each time. The organic phases were washed with 20 ml of saturated sodium chloride solution, dried over magnesium sulphate and concentrated. A single recrystallization of the product from hexane gave 91 mg (59%) of (4aαH,8aβH)-decahydro-2α-phenyl-6β-hydroxynaphthalene as colorless needles; m.p. 130.0°–132.5° C. Rf values [toluene/ethyl acetate (3:1)]: educt 0.75, product 0.19.

EXAMPLE 15

(a) 22.6 g of (methoxymethyl)-triphenylphosphonium chloride were suspended in 75 ml of t-butyl methyl ether at −10° C. while gassing with argon in a 350 ml sulphonation flask fitted with a dropping funnel, thermometer and solid substance addition tube with a Teflon skin and treated portionwise with 7.9 g of solid potassium t-butylate. After completion of the addition, the mixture was stirred at 0°–5° C. for a further 30 minutes and then the deep orange, partially heterogeneous mixture was treated dropwise (within 10 minutes) with a solution of 10 g of (4aβH,8aαH)-decahydro-2-oxo-6α-phenylnaphthalene (prepared according to Example 1; purity 95%) in 40 ml of t-butyl methyl ether. In so doing the internal temperature should not exceed 5° C. After completion of the addition, the now ochre colored mixture was warmed to 25° C. and stirred for a further 1 hour, whereby it again became pale orange colored. After adding 150 ml of a 2% sodium bicarbonate solution, the mixture was filtered and then the aqueous phase was separated and extracted a further twice with 100 ml of ether each time. The organic phases were washed with 100 ml of water, dried over magnesium sulphate and concentrated. The semi-crystalline residue was suspended in 500 ml of hexane at 50° C., subsequently cooled to −20° C. and freed from precipitated triphenylphosphine oxide by filtration. Concentration and drying in a high vacuum gave 12.0 g of an almost colorless oil (purity 93%) which was heated to reflux for 1 hour in 100 ml of tetrahydrofuran/2 N hydrochloric acid (4:1). The cooled mixture was poured into 100 ml of water and extracted three times with 100 ml of ether each time. The organic phases were washed twice with 100 ml of water each time, dried over magnesium sulphate and concentrated. There were obtained 12.0 g of a yellowish, viscous oil (purity 91%) which was an 8:2 mixture of the (4aβH,8aαH)-decahydro-6α-phenyl-2β-naphthalenecarboxaldehyde and the -2α-naphthalenecarboxaldehyde in accordance with gas chromatography and NMR spectrum. This material was used in the following reduction step without further purification. Rf values [hexane/ether (9:1)]: enol ether 0.38, (4aβH,8aαH)-decahydro-6α-phenyl-2β-naphthalenecarboxaldehyde 0.17, (4aβH,8aαH)-decahydro-6α-phenyl-2α-naphthalenecarboxaldehyde 0.12.

(b) A solution of 12.0 g of the foregoing crude aldehyde mixture in 150 ml of 0.1 N methanolic potassium hydroxide solution was placed at 0° C. while gassing with argon in a 500 ml round flask fitted with a thermometer and solid substance addition tube with a Teflon skin and treated portionwise during 20 minutes with 0.95 g of solid sodium borohydride, a white precipitate gradually forming. After completion of the addition, the mixture was stirred at 0° C. for a further 20 minutes, then 200 ml of water were added and the mixture was extracted three times with 200 ml of methylene chloride each time. The organic phases were washed twice with 100 ml of water each time, dried over magnesium sulphate and concentrated. The resulting, crystalline (4aβH,8aαH)-decahydro-2β-(hydroxymethyl)-6α-phenylnaphthalene (11.25 g; purity 93%) was used in the following tosylation step without additional purification. By a single crystallization from hexane there was obtained a purity of 99.0%; m.p. 96°–98° C.; Rf value [toluene/ethyl acetate (9:1)]: 0.21.

(c) A mixture of 11.25 g of the foregoing crude product containing (4aβH,8aαH)-decahydro-2β-(hydroxymethyl)-6α-phenylnaphthalene in 10 ml of pyridine was placed at 0° C. while gassing with argon in a 100 ml round flask fitted with a thermometer and dropping funnel and treated within 5 minutes with a solution of 14.5 g of tosyl chloride in 15 ml of pyridine. The cooling bath was removed and the mixture was stirred at room temperature overnight. Ice was then added, the mixture was made acid with 25 ml of concentrated hydrochloric acid and extracted three times with 100 ml of methylene chloride each time. The organic phases were washed twice with 100 ml of water each time, dried over magnesium sulphate and concentrated. Recrystallization of the resulting crystalline mass (18.4 g) from 350 ml of methanol gave 11.70 g of (4aβH,8aαH)-decahydro-6α-phenyl-2β-(tosyloxymethyl)naphthalene as colourless, long needles; m.p. 88.0°–88.8° C. From the mother liquor, concentrated to 100 ml, there could be obtained 2.17 g of crystalline material which yielded a further 1.55 g of pure tosylate after additional crystallization from 45 ml of methanol. Total yield 13.25 g [79.7% based on (4aβH,8aαH)-decahydro-2-oxo-6α-phenylnaphthalene]. Rf value [toluene/ethyl acetate 9:1)]: 0.58.

(d) 28 ml of a 2.14 M solution of ethylmagnesium bromide in ether were placed under an argon atmosphere at −60° C. in a 200 ml sulphonation flask fitted with a stirrer, thermometer and dropping funnel, diluted with 20 ml of absolute tetrahydrofuran and treated dropwise with 6 ml of a 0.1 M solution of lithium tetrachlorocuprate in absolute tetrahydrofuran, as well as subsequently with a solution of 7.97 g of (4aβH,8aαH)-decahydro-6α-phenyl-2β-(tosyloxymethyl)naphthalene in 20 ml of absolute tetrahydrofuran so that the internal temperature did not exceed −55° C. After completion of the addition, the mixture was stirred at −15° C. for 63 hours, treated cautiously with 20 ml of 2 N sulphuric acid and extracted three times with 100 ml of hexane each time. The organic phases were washed twice with 50 ml of water each time, dried over magnesium sulphate and concentrated. Chromatography of the crude product on a short column of silica gel using hexane as the eluant gave 4.50 g (89%) of (4aαH,8aβH)-decahydro-6β-propyl-2α-phenylnapthalene as colorless crystals (purity 99.0%). Additional crystallization from methanol yielded analytically pure material; m.p. 61.2° C.; Rf value (hexane): 0.41.

EXAMPLE 16

460 mg of sodium hydride in 10 ml of dimethylformamide were placed at room temperature while gassing with argon in a sulphonation flask fitted with a thermometer and dropping funnel and treated with a solution of 392 mg of (4aαH,8aβH)-decahydro-2α-(p-pentylphenyl)-6β-hydroxynaphthalene in 10 ml of dimethylformamide and then with 1.52 ml of n-butyl iodide. After completion of the addition, the brown-green, heterogeneous mixture was stirred at 50° C. for a further 3 days before it was poured cautiously into 100 ml of water and extracted three times with 150 ml of hexane each time. The organic phases were washed a further three times with 150 ml of water each time, dried over magnesium sulphate and concentrated. Low-pressure chromatography of the residue on silica gel with hexane and 2% ether/hexane as well as recrystallization from methanol gave (4aαH,8aβH)-decahydro-2α-(p-pentylphenyl)-6β-butyloxynaphthalene as colorless crystals; m.p. 37°–38° C.; Rf value [hexane/ether (19:1)]: 0.23.

The (4aαH,8aβH)-decahydro-2α-(p-pentylphenyl)-6β-hydroxynaphthalene used as the starting material was prepared as follows:

(a) A mixture of 10.0 g of (4aβH,8aαH)-decahydro-2-oxo-6α-phenylnaphthalene (prepared according to Example 1) and 6.3 ml of n-valeroyl chloride in 1 l of methylene chloride was placed at 0° C. while gassing with argon in a sulphonation flask fitted with a dropping funnel, thermometer and solid substance addition tube and treated portionwise with 14.6 g of aluminium chloride. After completion of the addition (about 10 minutes), the orange-brown mixture was stirred at 0° C. for a further 5 minutes and then at room temperature for 18 hours. Subsequently, the flask content was poured cautiously into 1 l of ice-water and extracted a further twice with 500 ml of methylene chloride each time. The organic phases were washed once with 500 ml of 2 N hydrochloric acid and twice with 500 ml of water each time, dried over magnesium sulphate and concentrated. Low-pressure chromatography (0.5 bar) of the brown oily residue on silica gel with 10% ethyl acetate/petroleum ether gave 11.3 g (83%) of (4aβH,8aαH)-decahydro-6α-(p-valerylphenyl)naphthalene-2-one as a yellow oil in a purity of 94%; Rf values [toluene/ethyl acetate (3:1)]: educt 0.45, product 0.37.

(b) 2.70 g of (4aβH,8aαH)-decahydro-6α-(p-valerylphenyl)naphthalen-2-one (purity 91%) dissolved in 80 ml of absolute ethanol were hydrogenated in a sulphonation flask in the presence of 300 mg of prehydrogenated 10% palladium-on-carbon at normal pressure and room temperature for 5 hours (hydrogen uptake 380 ml). Filtration and concentration of the mixture gave 2.30 g of a yellowish oil which was dissolved in 40 ml of diethyl ether and added dropwise within 10 minutes to a suspension of 640 mg of lithium aluminium hydride in 10 ml of diethyl ether. After completion of the addition, the mixture was stirred at room temperature for a further 30 minutes, then added cautiously to 50 ml of 2 N sulphuric acid and extracted three times with 50 ml of diethyl ether each time. The organic phases were washed a further twice with 50 ml of water each time, dried over magnesium sulphate and concentrated. A single crystallization of the semi-crystalline residue (1.9 g) from hexane gave 480 mg of (4aαH,8aβH)-decahydro-2α-(p-pentylphenyl)-6β-hydroxynaphthalene as colorless crystals in a purity of

EXAMPLE 17

A mixture of 10.5 g of (4aαH,8aβH)-decahydro-6β-pentyl-2α-(p-iodophenyl)naphthalene and 3.6 g of copper (I) cyanide in 100 ml of dimethylformamide was heated to reflux for 18 hours while gassing with argon in a round flask fitted with a reflux condenser. The cooled mixture was subsequently poured into 70 ml of 25% ammonium chloride solution and extracted three times with 150 ml of hexane each time. The organic phases were washed a further three times with 100 ml of water each time, dried over magnesium sulphate and concentrated. Low-pressure chromatography (0.5 bar) of the residue (7.59 g) on silica gel with 3% ethyl acetate/petroleum ether gave 7.20 g (91%) of p-[(4aαH,8aβH)-decahydro-6β-pentyl-2α-naphthyl]-benzonitrile as colorless crystals in a purity of 98.3%. Recrystallization from 40 ml of acetone finally gave 6.13 g of product with m.p. 72.8° C. and cl.p. 125.1° C.; Rf value (3% ethyl acetate/petroleum ether): 0.34.

The (4aαH,8aβH)-decahydro-6β-pentyl-2α-(p-iodophenyl)-naphthalene used as the starting material was prepared as follows:

A mixture of 10.0 g of (4aαH,8aβH)-decahydro-6β-pentyl-2α-phenylnaphthalene (prepared according to Example 1), 1.4 g of iodic acid, 3.6 g of iodine, 47 ml of acetic acid, 13 ml of water, 13 ml of carbon tetrachloride and 2 ml of concentrated sulphuric acid was heated to reflux for 18 hours while gassing with argon in a round flask. Subsequently, the brown-orange mixture was poured into 50 ml of 10% sodium thiosulphate solution and extracted three times with 100 ml of hexane each time. The organic phases were washed twice with 100 ml of water each time, dried over magnesium sulphate and concentrated. The thus-obtained residue (15.25 g) contained 79.9% of (4aαH,8aβH)-decahydro-6β-pentyl-2α-(p-iodophenyl)naphthalene, 15.9% of (4aαH,8aβH)-decahydro-6β-pentyl-2α-(o-iodophenyl)-naphthalene and 3.2% of educt in accordance with gas chromatographical analysis. A crystallization from 120 ml of acetone gave 10.5 g (73%) of (4aαH,8aβH)-decahydro-6β-pentyl-2α-(p-iodophenyl)naphthalene as colorless crystals in a purity of 99.1%; m.p. 89.3° C.; Rf value (hexane): 0.45.

The following compounds can be prepared in an analogous manner:

p-[(4aαH,8aβH)-Decahydro-6β-methyl-2α-naphthyl]benzonitrile; m.p. 88.5° C., cl.p. 73.9° C. (monotropic).

p-[(4aαH,8aβH)-Decahydro-6β-ethyl-2α-naphthyl]-benzonitrile; m.p. 74.5° C., cl.p. 95.5° C.

p-[(4aαH,8aβH)-Decahydro-6β-propyl-2α-naphthyl]benzonitrile; m.p. 77.3° C., cl.p. 126.5° C.

p-[(4aαH,8aβH)-Decahydro-6β-butyl-2α-naphthyl]-benzonitrile; m.p. 61.3° C., cl.p. 116° C.

p-[(4aαH,8aβH)-Decahydro-6β-heptyl-2α-naphthyl]benzonitrile; m.p. 78.6° C., cl.p. 117.5° C.

(4aαH,8aβH)-Decahydro-6β-methyl-2α-(p-iodophenyl)-naphthalene; m.p. 88.1° C.

(4aαH,8aβH)-Decahydro-6β-ethyl-2α-(p-iodophenyl)-naphthalene; m.p. 77.5° C., (4aαH,8aβH)-Decahydro-6β-propyl-2α-(p-iodophenyl)-naphthalene; m.p. 93.1° C.

(4aαH,8aβH)-Decahydro-6β-butyl-2α-(p-iodophenyl)-naphthalene; m.p. 55.0° C.

(4aαH,8aβH)-Decahydro-6β-heptyl-2α-(p-iodophenyl)-naphthalene; m.p. 87.4° C.

EXAMPLE 18

40 mol % of 4'-heptyl-4-cyanobiphenyl,
23 mol % of trans-4-butylcyclohexanecarboxylic acid p-ethoxyphenyl ester,
21 mol % of trans-4-pentylcyclohexanecarboxylic acid p-methoxyphenyl ester,
16 mol % of (4aαH,8aβH)-decahydro-2α-(trans-4-pentylcyclohexyl)-6β-pentylnaphthalene, cl.p. 76° C.

EXAMPLE 19

17 mol % of 4'-heptyl-4-cyanobiphenyl,
30 mol % of p-(trans-4-pentylcyclohexyl)benzonitrile,
17 mol % of trans-4-butylcyclohexanecarboxylic acid p-ethoxyphenyl ester,
16 mol % of trans-4-pentylcyclohexanecarboxylic acid p-methoxyphenyl ester,
7 mol % of p-[5-(trans-4-pentylcyclohexyl)-2-pyrimidinyl]-benzonitrile,
13 mol % of (4aαH,8aβH)-decahydro-2α-(trans-4-pentylcyclohexyl)-6β-pentylnaphthalene, cl.p. 76.6°–77.5° C.

EXAMPLE 20

5 mol % of p-(5-pentyl-2-pyrimidinyl)benzonitrile,
8 mol % of p-(5-heptyl-2-pyrimidinyl)benzonitrile,
15 mol % of trans-4-butylcyclohexanecarboxylic acid p-ethoxyphenyl ester,
14 mol % of trans-4-pentylcyclohexanecarboxylic acid p-methoxyphenyl ester,
33 mol % of p-[2-(trans-4-pentylcyclohexyl)-1-ethyl]-benzonitrile,
15 mol % of 4'-[(4aαH,8aβH)-decahydro-6β-methyl-2α-naphthyl]valerophenone,
5 mol % of 4'-[(4aαH,8aβH)decahydro-6β-propyl-2α-naphthyl]-propiophenone,
5 mol % of 4'-[(4aαH,8aβH)-decahydro-6β-pentyl-2α-naphthyl]butyrophenone,
m.p. < −10° C., cl.p. 55.1°–55.2° C.

EXAMPLE 21

4 mol % of p-(5-pentyl-2-pyrimidinyl)benzonitrile,
6 mol % of p-(5-heptyl-2-pyrimidinyl)benzonitrile,
12 mol % of trans-4-butylcyclohexanecarboxylic acid p-ethoxyphenyl ester,
11 mol % of trans-4-pentylcyclohexanecarboxylic acid p-methoxyphenyl ester,
29 mol % of p-[2-(trans-4-pentylcyclohexyl)-1-ethyl]-benzonitrile,
6 mol % of 6-butyl-trans-decalin-2-carboxylic acid trans-4-pentylcyclohexyl ester,
12 mol % of 4'-[(4aαH,8aβH)-decahydro-6β-methyl-2α-naphthyl]-valerophenone,
3 mol % of 4'-[(4aαH,8aβH)-decahydro-6β-propyl-2α-naphthyl]-propiophenone,
17 mol % of 4'-[(4aαH,8aβH)-decahydro-6β-propyl-2α-naphthyl]valerophenone,
m.p. < −10° C., cl.p. 71° C.

EXAMPLE 22

8 mol % of p-(5-pentyl-2-pyrimidinyl)benzonitrile,
14 mol % of p-(5-heptyl-2-pyrimidinyl)benzonitrile,
24 mol % of trans-4-butylcyclohexanecarboxylic acid p-ethoxyphenyl ester,
22 mol % of (4aαH,8aβH)-decahydro-2α-(p-heptylphenyl)-6β-propylnaphthalene, 17 mol % of (4aαH,8aβH)-decahydro-2α-(p-propyl-phenyl)-6β-pentylnaphthalene,
15 mol % of (4aαH,8aβH)-decahydro-2α-(p-pentyl-phenyl)-6β-pentylnaphthalene,
m.p. < −10° C., cl.p. 52.5° C.

EXAMPLE 23

6 mol % of p-(5-pentyl-2-pyrimidinyl)benzonitrile,
12 mol % of p-(5-heptyl-2-pyrimidinyl)benzonitrile,
8 mol % of p-[(4aαH,8aβH)-decahydro-6β-ethyl-2α-naphthyl]benzonitrile,
8 mol % of p-[(4aαH,8aβH)-decahydro-6β-propyl-2α-naphthyl]benzonitrile,
7 mol % of p-[(4aαH,8aβH)-decahydro-6β-pentyl-2α-naphthyl]-benzonitrile,
14 mol % of (4aαH,8aβH)-decahydro-2α-(p-propyl-phenyl)-6β-pentylnaphthalene,
23 mol % of (4aαH,8aβH)-decahydro-2α-(p-butyl-phenyl)-6β-pentylnaphthalene,
22 mol % of (4aαH,8aβH)-decahydro-2α-(p-pentyl-phenyl)-6β-pentylnaphthalene,
m.p. < −10° C., cl.p. 60.3°–60.5° C.

EXAMPLE 24

22 mol % of 4′-heptyl-4-cyanobiphenyl,
21 mol % of trans-4-butylcyclohexanecarboxylic acid p-ethoxyphenyl ester,
19 mol % of trans-4-pentylcyclohexanecarboxylic acid p-methoxyphenyl ester,
23 mol % of 4′-[(4aαH,8aβH)-decahydro-6β-propyl-2α-naphthyl]valerophenone,
15 mol % of (4aαH,8aβH)-decahydro-2α-(trans-4-pentylcyclohexyl)-6β-pentylnaphthalene, cl.p. 79.0°–79.4° C.

EXAMPLE 25

12 mol % of 4′-heptyl-4-cyanobiphenyl,
24 mol % of p-(trans-4-pentylcyclohexyl)benzonitrile,
13 mol % of p-(trans-4-heptylcyclohexyl)benzonitrile,
13 mol % of trans-4-butylcyclohexanecarboxylic acid p-ethoxyphenyl ester,
12 mol % of trans-4-pentylcyclohexanecarboxylic acid p-methoxyphenyl ester,
10 mol % of (4aαH,8aβH)-decahydro-2α-(trans-4-pentylcyclohexyl)-6β-pentylnaphthalene,
16 mol % of 4′-[(4-aαH,8aβH)-decahydro-6β-propyl-2α-naphthyl]valerophenone. cl.p. 68.0°–68.1° C.

EXAMPLE 26

32 mol % of (4aαH,8aβH)-decahydro-2α-(p-ethyl-phenyl)-6β-pentylnaphthalene,
23 mol % of (4aαH,8aβH)-decahydro-2α-(p-butyl-phenyl)-6β-pentylnaphthalene,
22 mol % of (4aαH,8aβH)-decahydro-2α-(p-pentyl-phenyl)-6β-pentylnaphthalene,
23 mol % of 4′-[(4aαH,8aβH)-decahydro-6β-propyl-2α-naphthyl]valerophenone, m.p. < −10° C., cl.p. 60.5°–60.6° C.

EXAMPLE 27

9 mol % of p-[(4aαH,8aβH)-decahydro-6β-propyl-2α-naphthyl]benzonitrile,
7 mol % of p-[(4aαH,8aβH)-decahydro-6β-pentyl-2α-naphthyl]benzonitrile,
35 mol % of (4aαH,8aβH)-decahydro-2α-(p-ethyl-phenyl)-6β-pentylnaphthelene,
25 mol % of (4aαH,8aβH)-decahydro-2α-(p-butyl-phenyl)-6β-pentylnaphthalene,
24 mol % of (4aαH,8aβH)-decahydro-2α-(p-pentyl-phenyl)-6β-pentylnaphthalene, m.p. < −10° C., cl.p. 57.3°–57.5° C.

EXAMPLE 28

19 mol % of trans-4-butylcyclohexanecarboxylic acid p-ethoxyphenyl ester,
18 mol % of trans-4-pentylcyclohexanecarboxylic acid p-methoxyphenyl ester,
8 mol % of p-[(4aαH,8aβH)-decahydro-6β-propyl-2α-naphthyl]benzonitrile,
5 mol % of p-[(4aαH,8aβH)-decahydro-6β-pentyl-2α-naphthyl]-benzonitrile,
30 mol % of (4aαH,8aβH)-decahydro-2α-p-ethyl-phenyl)-6β-pentylnaphthaline
20 mol % of (4aαH,8aβH)-decahydro-2α-(p-pentyl-phenyl)-6β-pentylnaphthalene, m.p. < −10° C., cl.p. 62.6°–62.7° C.

EXAMPLE 29

6 mol % of p-[(4aαH,8aβH)-decahydro-6β-propyl-2α-naphthyl]benzonitrile,
4 mol % of p-[(4aH,8aβH)-decahydro-6β-pentyl-2α-naphthyl]benzonitrile,
25 mol % of (4aαH,8aβH)-decahydro-2α-(p-ethyl-phenyl)-6β-pentylnaphthalene,
17 mol % of (4aαH,8aβH)-decahydro-2α-(p-butyl-phenyl)-6β-pentylnaphthalene,
17 mol % of (4aαH,8aβH)-decahydro-2α-(p-pentyl-phenyl)-6β-pentylnaphthalene,
19 mol % of 4′-[(4aαH,8aβH)-decahydro-6β-propyl-2α-naphthyl]valerophenone,
12 mol % of (4aαH,8aβH)-decahydro-2α-(trans-4-pentylcyclohexyl)-6β-pentylnaphthalene, cl.p. 73.7°–74.2.

We claim:

1. A compound of the formula

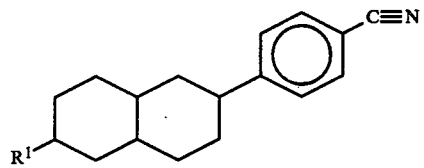

I wherein $R^1$ is hydrogen, methyl, —CH$_2$R, —OR or —CH$_2$OR, R is alkyl; and $R^1$ has up to 12 carbon atoms, its racemates or its optically active antipodes.

2. The compound of claim 1, wherein R is straight-chain alkyl.

3. The compound of claim 1 wherein $R^1$ is methyl, —CH$_2$R or —OR.

4. The compound of claim 3, wherein $R^1$ is methyl or —CH$_2$R.

5. The compound of claim 1 wherein $R^1$ has at most 9 carbon atoms.

6. The compound of claim 5 wherein $R^1$ has at most 7 carbon atoms.

7. The compound of claim 1 wherein $R^1$ is propyl, butyl, pentyl or heptyl.

8. The compound of claim 1 in racemic form.

9. An electro-optical cell containing a compound of the formula

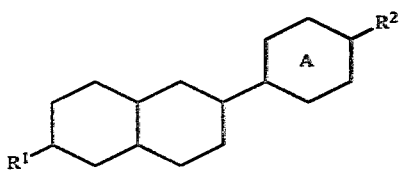

wherein $R^1$ is hydrogen, methyl, —$CH_2R$, —OR or —$CH_2OR$, R is alkyl; and $R^1$ has up to 12 carbon atoms, its racemates or its optically active antipodes.

10. A liquid crystalline mixture comprising at least two compounds at least one being a compound of the formula

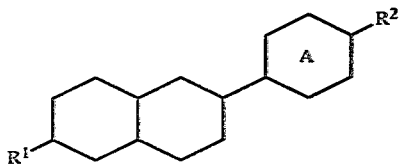

wherein $R^1$ is hydrogen, methyl, —$CH_2R$, —OR or —$CH_2OR$, R is alkyl; and $R^1$ has up to 12 carbon atoms, its racemates or its optically active antipodes.

11. The liquid crystalline mixture of claim 10 comprising a compound of the formula

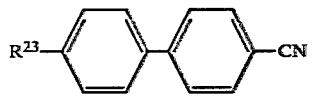

wherein $R^{23}$ is straight-chain alkyl or alkoxy of 2 to 7 carbon atoms.

12. The liquid crystalline mixture of claim 10 comprising a compound of the formula

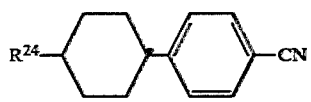

wherein $R^{24}$ is straight-chain alkyl of 3 to 7 carbon atoms.

13. The liquid crystalline mixture of claim 10 comprising a compound of the formula

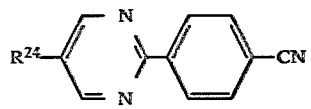

wherein $R^{24}$ is straight-chain alkyl of 3 to 7 carbon atoms.

14. The liquid crystalline mixture of claim 10 comprising a compound of the formula

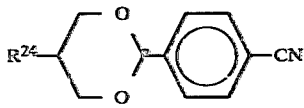

wherein $R^{24}$ is straight-chain alkyl of 3 to 7 carbon atoms.

15. The liquid crystalline mixture of claim 10 comprising a compound of the formula

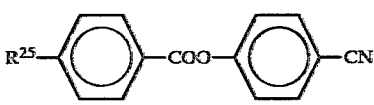

wherein $R^{25}$ is straight-chain alkyl of 2 to 7 carbon atoms.

16. The liquid crystalline mixture of claim 10 comprising a compound of the formula

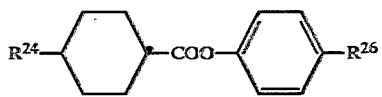

wherein $R^{24}$ is straight-chain alkyl of 3 to 7 carbon atoms and $R^{26}$ is cyano or straight-chain alkoxy of 1 to 3 carbon atoms.

17. The liquid crystalline mixture of claim 10 comprising a compound of the formula

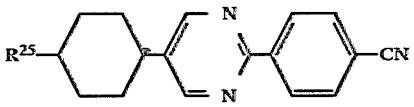

wherein $R^{25}$ is straight-chain alkyl of 2 to 7 carbon atoms.

18. The liquid crystalline mixture of claim 10 comprising a compound of the formula

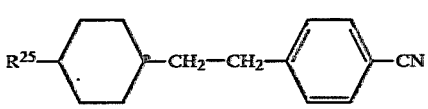

wherein $R^{25}$ is straight-chain alkyl of 2 to 7 carbon atoms.

* * * * *

UNITED STATES PATENT AND TRADEMARK OFFICE
CERTIFICATE OF CORRECTION

PATENT NO. : 4,432,885
DATED : February 21, 1984
INVENTOR(S) : Martin Petrzilka, Kuno Schleich It is certified that error appears in the above-identified patent and that said Letters Patent are hereby corrected as shown below:

Column 63, line 5 and line 20 delete structural formula, each occurrance and insert the following in place thereof:

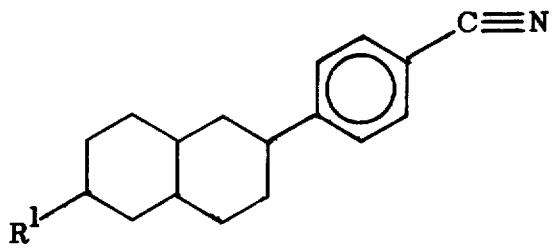

I

Signed and Sealed this

Thirty-first Day of July 1984

[SEAL]

Attest:

GERALD J. MOSSINGHOFF

Attesting Officer

Commissioner of Patents and Trademarks